US008703143B2

(12) United States Patent
Neri et al.

(10) Patent No.: US 8,703,143 B2
(45) Date of Patent: Apr. 22, 2014

(54) ANTIBODIES OF THE ED-B DOMAIN OF FIBRONECTIN, THEIR CONSTRUCTION AND USES

(75) Inventors: Dario Neri, Zurich (CH); Barbara Carnemolla, Genoa (IT); Luciano Zardi, Genoa (IT); Gregory Paul Winter, Cambridge (GB)

(73) Assignee: Philogen S.p.A., Siena (IT)

( * ) Notice: Subject to any disclaimer, the term of this patent is extended or adjusted under 35 U.S.C. 154(b) by 1442 days.

(21) Appl. No.: 11/842,774

(22) Filed: Aug. 21, 2007

(65) Prior Publication Data

US 2008/0274099 A1   Nov. 6, 2008

Related U.S. Application Data

(62) Division of application No. 09/194,356, filed as application No. PCT/GB97/01412 on May 23, 1997, now Pat. No. 7,273,924.

(30) Foreign Application Priority Data

May 24, 1996  (GB) .................................. 9610967.3

(51) Int. Cl.
| A61K 31/00 | (2006.01) |
| A61K 38/00 | (2006.01) |
| A61K 39/00 | (2006.01) |
| A61K 39/395 | (2006.01) |

(52) U.S. Cl.
USPC ....... 424/184.1; 424/9.1; 424/9.2; 424/130.1; 424/133.1; 424/134.1; 424/135.1; 424/136.1; 424/138.1; 424/141.1; 424/142.1; 424/155.1; 424/178.1; 424/183.1; 514/1; 514/1.1; 514/1.3; 514/19.2; 514/19.3; 514/19.4; 530/350; 530/380; 530/385; 530/386; 530/387.1; 530/387.3; 530/387.7

(58) Field of Classification Search
None
See application file for complete search history.

(56) References Cited

U.S. PATENT DOCUMENTS

| 4,894,326 A | 1/1990 | Matsuura et al. |
| 5,177,015 A | 1/1993 | Matsuura et al. |
| 5,243,029 A | 9/1993 | Matsuura et al. |
| 5,523,229 A | 6/1996 | Feinberg et al. |
| 5,648,485 A | 7/1997 | Dolphin et al. |
| 5,710,134 A | 1/1998 | Bosslet et al. |
| 5,734,025 A | 3/1998 | Komai et al. |
| 5,747,452 A | 5/1998 | Ruoslahti et al. |
| 5,817,776 A | 10/1998 | Goodman et al. |
| 5,831,088 A | 11/1998 | Dolphin et al. |
| 5,837,813 A | 11/1998 | Ruoslahti et al. |
| 5,843,156 A | 12/1998 | Slepian et al. |
| 5,849,701 A | 12/1998 | Roberts et al. |
| 5,877,289 A | 3/1999 | Thorpe et al. |
| 5,913,884 A | 6/1999 | Trauner et al. |
| 5,976,535 A | 11/1999 | Fritzberg et al. |
| 6,004,555 A | 12/1999 | Thorpe et al. |
| 6,015,897 A | 1/2000 | Theodore et al. |
| 6,036,955 A | 3/2000 | Thorpe et al. |
| 6,051,230 A | 4/2000 | Thorpe et al. |
| 6,093,399 A | 7/2000 | Thorpe et al. |
| 6,140,470 A | 10/2000 | Garen et al. |
| 6,267,722 B1 | 7/2001 | Anderson et al. |
| 6,394,952 B1 | 5/2002 | Anderson et al. |
| 6,696,245 B2 | 2/2004 | Winter et al. |
| 6,749,853 B1 | 6/2004 | Thorpe et al. |
| 2004/0001790 A1 | 1/2004 | Hilger et al. |
| 2004/0013640 A1 | 1/2004 | Zardi et al. |

FOREIGN PATENT DOCUMENTS

| EP | 0120694 | 10/1984 |
| EP | 0125023 | 11/1984 |
| EP | 184187 | 6/1986 |
| EP | 0211047 | 2/1987 |
| EP | 239400 | 9/1987 |
| EP | 0344134 | 11/1989 |
| EP | 0371998 | 6/1990 |
| EP | 0396612 | 11/1990 |
| EP | 0550400 | 7/1993 |
| EP | 0731167 | 9/1996 |
| EP | 0760679 | 3/1997 |
| GB | 2188638 | 10/1987 |
| JP | 0276598 | 3/1990 |
| JP | 4169195 | 6/1992 |
| WO | WO9311161 | 6/1993 |
| WO | WO9413804 | 6/1994 |
| WO | WO 9623816 | 8/1996 |
| WO | WO 9745544 | 12/1997 |
| WO | WO 9958570 | 10/1999 |
| WO | WO 0162800 | 8/2001 |

OTHER PUBLICATIONS

Goldenberg, D.M. and Sharkey, R.M. Novel radiolabeled antibody conjugates. Oncogene 26: 3734-3744, 2007.*
Bodey, B. Genetically engineered antibodies for direct antineoplastic treatment and systematic delivery of various therapeutic agents to cancer cells. Expert Opin. Biol. Ther. 1(4): 603-617, 2001.*
Rudikoff, S., et al., "Single Amino Acid Substitution Altering Antigen-Binding Specificity," Proc. Natl. Acad. Sci. USA, vol. 79, pp. 1979-1983, Mar. 1982.
Neri et al,"Antibodies from phage display libraries as immunochemical reagents", Methods in molecular biology, Immunochemical protocols, $2^{nd}$ ed, pp. 475-500, vol. 80.
Bird et al, "Single-Chain antigen binding proteins", Science 242: 423-426, Oct. 21, 1988.

(Continued)

*Primary Examiner* — Alana Harris Dent
(74) *Attorney, Agent, or Firm* — Millen, White, Zelano & Branigan, P.C.

(57) ABSTRACT

According to the present invention there is provided a specific binding member which is specific for and binds directly to the ED-B oncofoetal domain of fibronectin (FN). The invention also provides materials and methods for the production of such binding members.

23 Claims, 9 Drawing Sheets

(56) References Cited

OTHER PUBLICATIONS

Figure 2A:
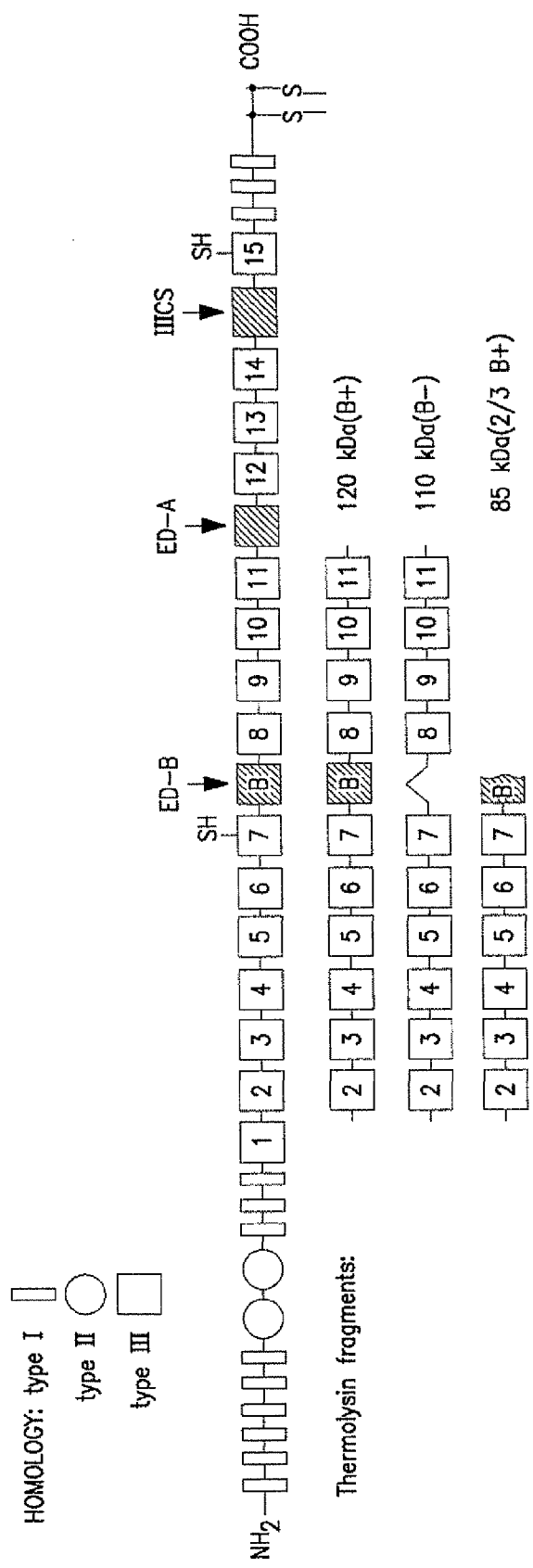

Clackson et al, "Making antibody fragments using phage display libraries", Nature 352: 624-628, Aug. 15, 1991.
L. Zardi et al, "Transformed human cells produce a new fibronectin isoform by preferential alternative splicing of a previously unobserved exon", The Embo Journal, vol. 6 No. 8, Aug. 1987, Cambridge, GB, pp. 2337-2342, XP002042100.
Carnemolla et al, "The inclusion of the type III repeat ED-B in the fibronectin molecule generates conformational modifications that unmask a cryptic sequence", The Journal of Biological Chemistry, vol. 267 No. 34, Dec. 5, 1992, Baltimore MD, USA, pp. 24689-24692, XP002042101.
Carnemolla et al, "Phage antibodies with pan-species recognition of the oncofoetal angiogenesis marker fibronectin ED-B domain", International Journal of Cancer, vol. 68 No. 3, 4, Nov. 1996, New York, NY USA, pp. 397-405, XP002042102.
Matsuura et al, "The oncofetal domain of fibronectin defined by monoclonal antibody FDC-6: Its presence in fibronectins from fetal and tumor tissues and its absence in those from normal adult tissues and plasma", Proc.Natl.Acad.Sci., vol. 82, pp. 6517-6521, Oct. 1985.
Matsuura et al, "An a-N-Acetylgalactosaminylation at the threonine residue of a defined peptide sequence creates the oncofetal peptide epitope in human fibronectin", The Journal of Biological Chemistry, vol. 264 No. 18, pp. 10472-10476, 1989.
Matsuura et al, "The oncofetal structure of human fibronectin defined by monoclonal antibody FDC-6", The Journal of Biological Chemistry, vol. 263 No. 7, pp. 3314-3322, 1988.
Isemura et al, "Isolation and Characterization of human placenta fibronectin", J. BioChem 96, 163-169, 1984.
J. Peters et al, "Expression of the alternatively spliced EIIIB segment of fibronectin", Cell Adhesion and Communication, vol. 3 No. 1, 1995, USA, pp. 67-89, XP002042097.
D. Zang et al, "Antibody specific for extra domain B of fibronectin demonstrates elevated levels of both extra domain B+ and B− fibronectin in osteoarthritic canine cartilage", Matrix Biology, vol. 14 No. 8, Oct. 1995, Stuttgart Germany, pp. 623-633, XP002042098.
Database WPI week 9017 Derwent Publications Ltd., London GB, AN 90-128252, XP002042103 & JP 02076598 A (Fujita Gakuen et al), Mar. 15, 1990.
Database WPI week 9231 Derwent Publications Ltd., London GB, AN 92-253398, XP002042104 & JP 04169195 A (Fujita Gakuen et al), Jun. 17, 1992.
P. Castellani et al, "The fibronectin isoform containing the ED-B oncofetal domain a marker of angiogenesis", International Journal of Cancer, vol. 59 No. 5, Dec. 1, 1994, New York, NY USA, pp. 612-618, XP002042099.
Epstein, "FDA regulation of HIV related tests and procedures", Aids testing a comprehensive guide to technical medical social legal and management issues, Eds. Schochetman and George, pp. 52-61, Springer Verlag, New York, 1994.
Korver et al, "Measurement of primary in vivo IgM and IgG antibody response to KLH in humans Implications of pre-immune IgM binding in antigen specific ELISA", Journal of Immunological methods, 1984, pp. 241-251, vol. 74.
Weir et al, "An immunoglobulin G1 monoclonal antibody highly specific to the wall of cryptosporidium oocysts", Clinical and diagnostic laboratory immunology, Sep. 2000, pp. 745-750, vol. 7 No. 5.
Nozawa et al, "HMMC-1 a humanized monoclonal antibody with therapeutic potential against mullerian duct related carcinomas", Clinical cancer research, Oct. 15, 2004, pp. 7071-7078, vol. 10.
23 slide, power point of Dr. Zardi, Feb. 2007.
Clayton A Buck and Jean Paul Thiery,"Cell of adhesion and communications" 1995, vol. 3, pp. 67-89, Harwood academic publishers Gmbh printed in the USA.
Patrizia Castellani et al,"The fibronectin isoform containing the ED-B oncofetal domain a marker of angiogenesis", 1994, vol. 59, pp. 612-618, publication of the international union against cancer, Genoa Italy.
Luciano Zardi et al, "Transformed human cells produce a new fibronectin isoform by preferential alternative splicing of a previously unobserved Exon", 1987, vol. 6, No. 8, pp. 2337-2342, The embo journal IRL press limited, Oxford England.
Barbara Carnemolla et al,"The inclusion of the type III repeat ED_R in the fibronectin molecule generates conformational modifications that unmask a cryptic sequence" 1992, vol. 267, No. 34, pp. 24689-24692, The journal of biological chemistry printed in the USA.
Barbara Carnemolla et al,"Phage antibodies with pan species recognition of the oncofetal angiogenesis marker fibronectin ED-B domain" 1996, vol. 68, pp. 397-405, publication of the international union against cancer, Genoa Italy.
Dai Wei Zang et al, "Antibody specific for extra domain B of fibronectin demonstrates elevated levels of both extra domain B+ and B− fibronectin in osteoarthritic canine cartilage", 1994. vol. 14, pp. 623-633, Gustav Fischer Verlag, Stuttgart-Jena New York.
Tomohiko Fukuda et al,"Mice lacking the EDB segment of fibronectin develop normally but exhibit reduced cell growth and fibronectin matrix assembly in vitro", Cancer research, Oct. 1, 2002, pp. 5603-5610, vol. 62.
Andrew Griffiths et al,"Isolation of high affinity human antibodies directly from large synthetic repertoires", The EMBO journal, 1994, pp. 3245-3260, vol. 13, No. 14.
Dario Neri et al,"Targeting by affinity matured recombinant antibody fragments of an angiogenesis associated fibronectin isoform", Nature biotechnology, vol. 15, Nov. 1997, pp. 1271-1275.
Dario Neri et al,"Affinity reagents against tumor associated extracellular molecules and newforming vessels", Advanced drug delivery reviews, Apr. 6, 1998, pp. 43-52, vol. 31, No. 1-2, XP002124780.
Pini A et al,"Design and use of a phage display library. Human antibodies with subnanomolar affinity against a marker of angiogenesis eluted from a two-dimensional gel", Journal of biological chemistry, Aug. 21, 1998, pp. 21769-21776, vol. 273, No. 34, XP002124781.
Viti F et al,"Increased binding affinity and valence of recombinant antibody fragments lead to improved targeting of tumoral angiogenesis", Cancer research, Jan. 15, 1999, pp. 347-352, vol. 59, No. 2, XP002124782.
R Fattorusso et al,"NMR structure of the human oncofetal fibronectin ED-B domain a specific marker for angiogenesis", Apr. 15, 1999, Structure, pp. 381-390, vol. 7, No. 4, XP002124783.
Tarli L et al,"A high affinity human antibody that targets tumoral blood vessels", Blood, Jul. 1, 1999, pp. 192-198, vol. 94, No. 1, XP002124784.
M Zalutsky et al,"Labeling monoclonal antibodies and F(ab')2 fragments with the alpha particle emitting nuclide astatine-211: preservation of immunoreactivity and in vivo localization", Proceedings of the National academy of Sciences in the USA, Sep. 1989, vol. 86, No. 18, pp. 7149-7153, XP002172060.
S Lindegren et al."Chloramine T in high specific activity radioiodination of antibodies using N succinimidyl-3-(trimehtylstannyl) benzoate as an intermediate", Nuclear Medicine and Biology, Oct. 1998, pp. 659-665, vol. 25, No. 7, XP004149436, Oxford.
M Birchler et al,"Selective targeting and photocoagulation of ocular angiogenesis mediated by a phage derived human antibody fragment", Nature biotechnology, Oct. 1999, pp. 984-988, vol. 17, No. 10, XP002172061, New York, NY USA.
Judah Folkman,"Angiogenesis in cancer vascular rheumatoid and other disease", Nature medicine, vol. 1, No. 1, 1995, pp. 27-31.
Renata Pasqualini et al,"a-Vintegrins as receptors for tumor targeting by circulating ligands", Nature biotechnology, vol. 15, Jun. 1997, pp. 542-546.
Michael S O'Reilly et al,"Angiostain induces and sustains dormancy of human primary tumors in mice", Nature Medicine, vol. 12, No. 6, Jun. 1996, pp. 689-692.
Xianming Huang et al,"Tumor infraction in mice by antibody directed targeting of tissue factor to tumor vasculature", Science, vol. 275, Jan. 24, 1997, pp. 547-550.
Dario Neri et al,"Biophysical methods for the determination of antibody-antigen affinities", Tibtech, vol. 14, Dec. 1996, pp. 465-470.
E Sally Ward et al,"Binding activities of a repetoire of singe immunoglobulin variable domains secreted from *Escherichia coli*", Nature, vol. 341, No. 6242, Oct. 12, 1989, pp. 544-546.

(56) References Cited

OTHER PUBLICATIONS

James S Huston et al,"Protein engineering of antibody binding sites recovery of specific activity in an anti-digoxin single chain Fv analogue produced in *Escherichia coli*", Proc. Natl. Acad. Sci. USA, vol. 85, Aug. 1988, pp. 5879-5883.
Phillip Holliger et al,"Diabodies small bivalent and bispecific antibody fragments", Proc. Natl. Acad. Sci. USA, vol. 90, Jul. 1993, pp. 6444-6448.
Phillip Holliger et al,"Engineering bispecific antibodies", Current opinion in biotechnology, vol. 4, No. 4, 1993, pp. 446-449.
Cyrus Chothia et al,"Canonical structures for the hypervariable regions of immunoglobulins", Journal of molecular biology, vol. 196, No. 4, Aug. 20, 1987, pp. 901-917.
D Neri et al,"Multipurpose high sensitivity luminescence analyzer LUANA; use in gel eiectrophoresis", Biotechniques, vol. 20, No. 4, Apr. 1996, pp. 708-712.
Ian M Tomlinson et al,"The repertoire of human germline Vh sequence reveals about fifty groups of Vh segments with different hypervariable loops", Academic press, vol. 227, No. 3, Oct. 5, 1992, pp. 776-798.
Johnathan P L Cox et al,"A directory of human germ line Vx segment reveals a strong bias in their usage", European journal of immunology Apr. 1994, pp. 827-836.
James D Marks et al,"By passing immunization human antibodies from V gene libraries displayed on phage", Journal of molecular biology, vol. 222, No. 3, Dec. 5, 1991, pp. 581-597.
Hennie R Hoogenboom et al,"Multi subunit proteins on the surface of filamentous phage methodologies for displaying antibody FAB heavy and light chains", Nucleic Acids research, vol. 19, No. 15, Aug. 11, 1991, pp. 4133-4137.
Dario Neri et al,"Radioactive labeling of recombinant antibody fragments by phosphorylation using human casein kinase II and [y-32P]-ATP", Nature biotechnology, vol. 14, No. 4, Apr. 1996, pp. 485-490.
Robert Schier et al,"Identification of functional and structural amino acid residues by parsimonious mutagenesis", Gene, vol. 169, 1996, No. 2, pp. 147-155.
Wataru Ito et al,"Mutations in the complementarity determining regions do not cause differences in free energy during the process of formation of the activated complex between an antibody and the corresponding protein antigen", Journal of molecular biology, vol. 248, No. 4, May 12, 1995, pp. 729-732.
C Hamers-Casterman et al,"Naturally occurring antibodies devoid of light chains", International weekly journal of science, vol. 363, No. 6428, Jun. 3, 1993, pp. 446-448.
U Jonsson et al,"Real time biospecific interaction analysis using surface plasmon resonance and sensor chip technology", Biotechniques, vol. 11, No. 5, Nov. 1991, pp. 620-627.
Ahuva Nissim et al,"Antibody fragments from a single pot phage display library as immunochemical reagents", The Embo journal, vol. 13, No. 3, Feb. 1, 1994, pp. 692-698.
Alessandro Pinni et al,"Hierarchial affinity maturation of a phage library derived antibody for the selective removal of cytomegalovirus from plasma", Journal of immunological methods, vol. 206, No. 1-2, 1997, pp. 171-182.
Daniel R Deaver,"A new non isotopic detection system for immunoassays", Nature, vol. 377, No. 6551, Oct. 26, 1995, pp. 758-760.
Matsuura H et al,"The oncofetal structure of human fibronectin defined by monoclonal antibody FDC-6; unique structural requirement for the antigenic specificity provided by a glycosylhexapeptide", Mar. 1988, J. Biol. Chem. 263, pp. 3314-3322.
Zheng M et al,"Synthetic immunochemistry of glyconexapeptide analogues characteristic of oncofetal fibronectin solid phase synthesis and antigenic activitiy", Int. J. Pept. Protein Res., 43, 230-238, Mar. 1994.
Feinberg et al,"Monoclonal antibody X18A4 identifies an oncofetal fibronectin eptiope distinct from the FDC-6 binding site", Am. J. Obstet. Gynecol 172, 1526-1536, May 1995.

Schick et al,"The synthesis and localization of alternatively spliced fibronectin EIIIB in resting and thrombin treated megakaryocytes", Blood, vol. 87, No. 5, Mar. 1, 1996, pp. 1817-1823.
White et al,"Chick cartilage fibronectin differs in structure from the fibronectin in limb mesenchyme", 1996, Exp. Cell Res., 224, pp. 391-402.
Mariani et al,"Tumor targeting potential of the monoclonal antibody vBC-1 against oncofetal fibronectin in nude mice bearing human tumor implants", The American cancer society, Dec. 15, 1997, pp. 2378-2384, vol. 80, No. 12.
Neri et al,"Antibodies from phage display libraries as immunochemical reagents", Methods in molecular biology, Immunochemical protocols, $2^{nd}$ ed, pp. 475-500, vol. 80, 1998.
Birchler et al, "Infrared photodetection for the in vivo localization of phage derived antibodies directed against angiogenic markers", Journal of immunological methods, 1999, pp. 239-248, vol. 231.
Nilsson et al,"Targeted delivery of tissue factor to the ED-B domain of fibronectin a marker of angiogenesis mediates the infraction of solid tumors in mice", Cancer research, Jan. 15, 2001, pp. 711-716, vol. 61.
Halin et al,"Antibody based targeting of angiogenesis", Critical reviews in therapeutic drug carriers systems, 2001, pp. 299-339, vol. 28, No. 3.
Giovannoni et al,"Isolation of anti-angiogenesis antibodies from a large combinatorial repertoire by colony filter screening", Nucleic acids research, 2001, vol. 9, No. 5, e27.
Demarti et al,"Selective targeting of tumor neovasculature by a radiohalogenated human antibody fragment specific for the ED-B domain of fibronectin", European journal of nuclear medicine, Apr. 2001, short communication, vol. 28, No. 4.
Carnemolla et al,"Enhancement of the antitumor properties of interleukin-2 by its targeted delivery to the tumor blood vessel extracellular matrix", Hemostatis Thrombosis and vascular biology blood, Mar. 1, 2002, pp. 1659-1665, vol. 99, No. 5.
Halin et al,"Enhancement of the antitumor properties of interleukin-12 by its targeted delivery to the tumor blood vessel extracellular matrix", Nature Biotechnology, Mar. 2002, pp. 264-269, vol. 20.
Marty et al,"Cytotoxic targeting of F9 teratocarcinoma tumors with anti ED-B fibronectin scFv antibody modified liposomes", British Journal of Cancer, 2002, pp. 106-112, vol. 87, Cancer research UK.
Melkko et al,"An antibody calmodulin fusion protein reveals a functional dependence between macromolecular isoelectric point and tumor targeting performance", Int. J. Radiation Oncology Biol. Phys., 2002, pp. 1485-1490, vol. 54, No. 5.
Castellani et al,"Differentiation between high and low grade astrocytoma using a human recombinant antibody to the extra domain B of fibronectin", American journal of pathology, Nov. 2002, 1695-1700, vol. 161, No. 5, American society for investigative pathology.
Borsi et al,"Selective targeting of tumoral vasculature comparison of different formats of an antibody L19 to the ED-B domain of fibronectin", Int. J. Cancer, 2002, pp. 75-85, vol. 102.
Santimaria et al,"Immunoscintigraphic detection of the ED-B domain of fibronectin a marker of angiogenesis in patients with cancer", Clinical cancer research, Feb. 2003, pp. 571-579, vol. 9.
Scheuermann et al,"Discovery and investigation of lead compounds as binders to the extra domain B of the angiogenesis marker fibronectin", Drug development research, 2003, pp. 268-282, vol. 58.
Halin et al,"Synergistic therapeutic effects of a tumor targeting antibody fragment, fused to interleukin 12 and to tumor necrosis factor a", Cancer research, Jun. 15, 2003, pp. 3202-3210, vol. 63.
Borsi et al,"Selective targeted delivery of TNFa to tumor blood vessels", Blood first edition paper, prepublished online Aug. 21, 2003, American society of hematology, DOI 10.1182/blood-2003-04-1039.
Nicolo et al,"Expression of extradomain-B-containing fibronectin in subretinal choroidal neovascular membranes", 2003, Elsevier science inc.
Viti et al,"Recombinant antibodies for the selective targeting of tumor neovasculature", Current opinion in drug discovery and development, 2002, pp. 204-213, vol. 5, No. 2.

(56) References Cited

OTHER PUBLICATIONS

Viti et al,"Phage display libraries as a source of tumor targeting agents", Chimia, 2001, pp. 206-211, vol. 55, ISSN 0009-4293, The academic polymer scene in Switzerland.

Neri et al,"New approaches to tumor targeting", Cancer radioinmunotherapy present and future, nuclear medicine department, Hospital "M.Bufalini", Cesena, Italy, Harwood academic publishers, 1999.

Birchler et al,"Expression of the extra domain B of fibronectin a marker of angiogenesis in head and neck tumors", Laryngoscope, Jul. 2003, pp. 1231-1237, vol. 113.

Peters et al,"Fibronectin isoform distribution in the mouse: II. Differential distribution of the alternatively spliced EIIIB, EIIIA, and V segments in the adult mouse", Cell adhesion and communication, 1996, pp. 127-148, vol. 4, No. 2.

Chevalier et al,"Increased expression of Ed-B containing fibronectin an embryonic isoform of fibronectin in human osteoarthritic cartilage", British Journal of Rheumatology, vol. 35(5), pp. 407-415, 1996.

Chevalier et al,"Presence of ED-A containing fibronectin in human articular cartilage from patients with osteoarthritis and rheumatoid arthritis", Journal of Rheumatology, vol. 23(6), pp. 1022-1030, Jun. 1996.

Koukoulis et al,"Immunolocalization of cellular fibronectins in the normal liver cirrhosis and hepatocellular carcinomea", Ultrastructural pathology, Jan.-Feb. 1995, vol. 19(1), pp. 37-43.

Moyano et al,"Fibronectin type III5 repeat contains a novel cell adhesion sequence KLDAPT which binds activated a4B1 and a4B7 integrins", Journal of biological chemistry, Oct. 3, 1997, vol. 272(40), pp. 24832-24836.

Yu et al,"Fibronectin exposes different domains after adsorption to a heparinized and an unheparinized poly vinyl chloride surface", Biomaterial, Mar. 1997, vol. 18(56), pp. 421-427.

Borsi et al,"Preparation of phage antibodies to the ED-A domain of human fibronectin", Exp. Cell. Res., May 1, 1998, vol. 240(2), pp. 244-251.

Kaczmarek et al, Int. J. Cancer, vol. 58, pp. 11-16, 1994.

Kirkham et al, J. Mol. Biol., 1999, pp. 909-915, vol. 285.

Manabe Ri-Ichiroh et al, Journal of Cell Biology, vol. 139(1), pp. 295-307, Oct. 6, 1997.

Mardon et al, Journal of Cell science, vol. 104, pp. 783-792, 1993.

Menzin et al, Cancer 1998, vol. 82, pp. 152-158.

Paolella et al, Nucleic acids research, vol. 16(8), pp. 3545-3557, 1988.

Staffa et al, The Journal of Biological Chemistry, 272(52), pp. 33394-33401, Dec. 1997.

Vartio et al,"Differential expression of the ED sequence containing form of cellular fibronectin in embryonic and adult human tissues", Journal of cell science, vol. 88, pp. 419-430, 1987.

Ueda et al,"Selective distribution of fibronectin to a tumor cell line", Cancer letters, vol. 31, pp. 261-265, 1986.

Mariani et al,"A pilot pharmacokinetic and immunoscintigraphic study with the technetium-99m labeled monocolonal antibody BC-1 directed against oncofetal fibronectin in patients with brain tumors", Cancer, Dec. 15, 1997, pp. 2484-2489, vol. 80, suppl. 12, ISSN 0008-543X, Journal code CLZ, abstract USA.

Carnemolla et al, Journal of Cell biology, vol. 108, pp. 1139-1148, 1989.

\* cited by examiner

```
                                    CDR1                          CDR2
               10         20         30         40         50         60
CGS1   QVQLVESGGGLVQPGGSLRLSCAVSGFTFS SYAMS WVRQAPGKGLEWVS AISGSGGSTYYADSVKG
CGS2   EVQLVESGGGLVQPGGSLRLSCAASGFTFS SYAMS WVRQAPGKGLEWVS AISGSGGSTYYADSVKG

CDR3
              70         80         90        98
CGS1   RFTISRDNSKNTLYLQMNSLRAEDTAVYYCAR SLPK           WGQGTLVTVSR  (SEQ ID NO: 8)
CGS2   RFTISRDNSKNTLYLQMNSLRAEDTAVYYCAR GVGAFRPYRKHE   WGQGTLVTVSR  (SEQ ID NO: 9)
```

FIG. 1A

```
                         CDR1                                    CDR2
            10          20                 30           40       50
CGS1  SSELTQDPAVSVALGQTVRITC  QGDSLRSYYAS  WYQQKPGQAPVLVIY  GKNNRPS
                                                       T
CGS2  SSELTQDPAVSVALGQTVRITC  QGDSLRSYYAS  WYQQKPGQAPVLVIY  GKNNRPS

CDR3
      60        70        80           90             100
CGS1  GIPDRFSGSSSGNTASLTITTGAQAEDEADYYC  NSSPVVLNGVV  FGGGIKLTVLG  (SEQ ID NO: 10)
                      I                                   T
CGS2  GIPDRFSGSSSGNTASLTTTGAQAEDEADYYC  NSSPFTHNLVV  FGGGIKLTVLG  (SEQ ID NO: 11)
                                            E                T
```

FIG. 1B

| | CGS-1 | CGS-2 | BC-1 | IST-6 |
|---|---|---|---|---|
| 1 rec FN 2-11 (B−) | − | − | − | + |
| 2 rec FN 2-11 (B+) | + | + | + | − |
| 3 rec FN 7-9 (B−) | − | − | − | + |
| 4 rec FN 7-9 (B+) | + | + | + | − |
| 5 fusion protein λED-B | − | + | − | − |
| 6 fusion protein λchFN 60 | − | + | − | − |

FIG. 3A

SEQUENCE LISTING

```
<160> NUMBER OF SEQ ID NOS: 16

<210> SEQ ID NO 1
<211> LENGTH: 12
<212> TYPE: PRT
<213> ORGANISM: Homo sapiens

<400> SEQUENCE: 1

Gly Val Gly Ala Phe Arg Pro Tyr Arg Lys His Glu
1               5                   10

<210> SEQ ID NO 2
<211> LENGTH: 11
<212> TYPE: PRT
<213> ORGANISM: Homo sapiens

<400> SEQUENCE: 2

Asn Ser Ser Pro Val Val Leu Asn Gly Val Val
1               5                   10

<210> SEQ ID NO 3
<211> LENGTH: 11
<212> TYPE: PRT
<213> ORGANISM: Homo sapiens

<400> SEQUENCE: 3

Asn Ser Ser Pro Phe Glu His Asn Leu Val Val
1               5                   10

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
```

-continued

```
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other

<400> SEQUENCE: 4
cttggtccct ccgccgaata ccacmnnmnn mnnmnnmnnm nnagaggagt tacagtaata      60
gtcagcctc                                                             69

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attgcttttc cttttttgcgg ccgcgcctag gacggtcagc ttggtccctc cgcc           54

<210> SEQ ID NO 6
<211> LENGTH: 6
<212> TYPE: PRT
<213> ORGANISM: Homo sapiens

<400> SEQUENCE: 6

Asp Ser Ser Gly Asn His
 1               5

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caggaaacag ctatgac                                                    17

<210> SEQ ID NO 8
<211> LENGTH: 113
<212> TYPE: PRT
<213> ORGANISM: Homo sapiens

<400> SEQUENCE: 8

Gln Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                                  65                  70                  75                  80
Leu Gln Met Asn Ser Leu Arg Ala Glu Asp Thr Ala Val Tyr Tyr Cys
                85                  90                  95

Ala Arg Ser Leu Pro Lys Trp Gly Gln Gly Thr Leu Val Thr Val Ser
            100                 105                 110

Arg

<210> SEQ ID NO 9
<211> LENGTH: 121
<212> TYPE: PRT
<213> ORGANISM: Homo sapiens

<400> SEQUENCE: 9

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Gly Ala Phe Arg Pro Tyr Arg Lys His Glu Trp Gly
            100                 105                 110

Gln Gly Thr Leu Val Thr Val Ser Arg
        115                 120

<210> SEQ ID NO 10
<211> LENGTH: 109
<212> TYPE: PRT
<213> ORGANISM: Homo sapiens

<400> SEQUENCE: 10

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Thr Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Val Val Leu Asn Gly
                85                  90                  95

Val Val Phe Gly Gly Gly Thr Lys Leu Thr Val Leu Gly
            100                 105

<210> SEQ ID NO 11
<211> LENGTH: 109
<212> TYPE: PRT
<213> ORGANISM: Homo sapiens

<400> SEQUENCE: 11

Ser Ser Glu Leu Thr Gln Asp Pro Ala Val Ser Val Ala Leu Gly Gln
```

-continued

```
                 1               5                  10                  15
              Thr Val Arg Ile Thr Cys Gln Gly Asp Ser Leu Arg Ser Tyr Tyr Ala
                              20                  25                  30

Ser Trp Tyr Gln Gln Lys Pro Gly Gln Ala Pro Val Leu Val Ile Tyr
                      35                  40                  45

Gly Lys Asn Asn Arg Pro Ser Gly Ile Pro Asp Arg Phe Ser Gly Ser
                  50                  55                  60

Ser Ser Gly Asn Thr Ala Ser Leu Thr Thr Thr Gly Ala Gln Ala Glu
              65                  70                  75                  80

Asp Glu Ala Asp Tyr Tyr Cys Asn Ser Ser Pro Phe Glu His Asn Leu
                              85                  90                  95

Val Val Phe Gly Gly Gly Thr Lys Leu Thr Val Leu Gly
                              100                 105
```

<210> SEQ ID NO 12
<211> LENGTH: 4
<212> TYPE: PRT
<213> ORGANISM: Homo sapiens

<400> SEQUENCE: 12

```
Ser Leu Pro Lys
1
```

<210> SEQ ID NO 13
<211> LENGTH: 8
<212> TYPE: PRT
<213> ORGANISM: Homo sapiens

<400> SEQUENCE: 13

```
Pro Val Val Leu Asn Gly Val Val
1               5
```

<210> SEQ ID NO 14
<211> LENGTH: 8
<212> TYPE: PRT
<213> ORGANISM: Homo sapiens

<400> SEQUENCE: 14

```
Pro Phe Glu His Asn Leu Val Val
1               5
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

```
His His His His His His
1               5
```

<210> SEQ ID NO 16
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Gly Cys Leu Thr Asp Thr Leu Gln Ala Phe Thr Asp Gln Leu Glu
1               5                   10                  15
```

```
Asp Glu Lys Ser Ala Leu Gln Thr Glu Ile Ala His Leu Leu Lys Glu
            20                  25                  30

Lys Glu Lys Leu Glu Phe Ile Leu Ala Ala His
        35                  40
```

ANTIBODIES OF THE ED-B DOMAIN OF FIBRONECTIN, THEIR CONSTRUCTION AND USES

This application is a divisional application of U.S. application Ser. No. 09/194,356, filed on Sep. 2, 1999, now U.S. Pat. No. 7,273,924, which was the National Stage of International Application No. PCT/GB97/01412 filed May 23, 1997.

BACKGROUND

This invention relates to specific binding members for a foetal isoform of fibronectin, ED-B, which is also expressed in the developing neovasculature of tumours, as demonstrated both by immunocytochemistry and by targeting of tumours in vivo. It also relates to materials and methods relating to such specific binding members.

The primary aim of most existing forms of tumour therapy is to kill as many constituent cells of the tumour as possible. The limited success that has been experienced with chemotherapy and radiotherapy relates to the relative lack of specificity of the treatment and the tendency to toxic side-effects on normal tissues. One way that the tumour selectivity of therapy may be improved is to deliver the agent to the tumour through a binding protein, usually comprising a binding domain of an antibody, with specificity for a marker antigen expressed on the surface of the tumour but absent from normal cells. This form of targeted therapy, loosely termed 'magic bullets', has been mainly exemplified by monoclonal antibodies (mAbs) from rodents which are specific for so-called tumour-associated antigens expressed on the cell surface. Such mAbs may be either chemically conjugated to the cytotoxic moiety (for example, a toxin or a drug) or may be produced as a recombinant fusion protein, where the genes encoding the mAb and the toxin are linked together and expressed in tandem.

The 'magic bullet' approach has had limited, although significant, effect in the treatment of human cancer, most markedly in targeting tumours of lymphoid origin, where the malignant cells are most freely accessible to the therapeutic dose in the circulation. However, the treatment of solid tumours remains a serious clinical problem, in that only a minute proportion of the total cell mass, predominantly the cells at the outermost periphery of the tumour, is exposed to therapeutic immunoconjugates in the circulation; these peripheral targets form a so-called 'binding site barrier' to the tumour interior (Juweid et al, 1992, *Cancer Res.* 52 5144-5153). Within the tumour, the tissue architecture is generally too dense with fibrous stroma and closely packed tumour cells to allow the penetration of molecules in the size range of antibodies. Moreover, tumours are known to have an elevated interstitial pressure owing to the lack of lymphatic drainage, which also impedes the influx of exogenous molecules. For a recent review of the factors affecting the uptake of therapeutic agents into tumours, see Jain, R (1994), *Sci. Am.* 271 58-65.

Although there are obvious limitations to treating solid tumours through the targeting of tumour-associated antigens, these tumours do have a feature in common which provides an alternative antigenic target for antibody therapy. Once they have grown beyond a certain size, tumours are universally dependent upon an independent blood supply for adequate oxygen and nutrients to sustain growth. If this blood supply can be interfered with or occluded, there is realistic potential to starve thousands of tumour cells in the process. As a tumour develops, it undergoes a switch to an angiogenic phenotype, producing a diverse array of angiogenic factors which act upon neighbouring capillary endothelial cells, inducing them to proliferate and migrate. The structure of these newly-formed blood vessels is highly disorganised, with blind endings and fenestrations leading to increased leakiness, in marked contrast to the ordered structure of capillaries in normal tissue. Induction of angiogenesis is accompanied by the upregulation of expression of certain cell surface antigens, many of which are common to the vasculature of normal tissues. Identifying antigens which are unique to neovasculature of tumours has been the main limiting factor in developing a generic treatment for solid tumours through vascular targeting. The antigen which is the subject of the present invention addresses this problem directly.

During tumour progression, the extracellular matrix of the surrounding tissue is remodelled through two main processes: (1) the proteolytic degradation of extracellular matrix components of normal tissue and (2) the de novo synthesis of extracellular matrix components by both tumour cells and by stromal cells activated by tumour-induced cytokines. These two processes, at steady state, generate a 'tumoral extracellular matrix', which provides a more suitable environment for tumour progression and is qualitatively and quantitatively distinct from that of normal tissues. Among the components of this matrix are the large isoforms of tenascin and fibronectin (FN); the description of these proteins as isoforms recognises their extensive structural heterogeneity which is brought about at the transcriptional, post-transcriptional and post-translational level (see below). It is one of the isoforms of fibronectin, the so-called B+ isoform (B-FN), that is the subject of the present invention.

Fibronectins (FN) are multifunctional, high molecular weight glycoprotein constituents of both extracellular matrix and body fluids. They are involved in many different biological processes such as the establishment and maintenance of normal cell morphology, cell migration, haemostasis and thrombosis, wound healing and oncogenic transformation (for reviews see Alitalo et al., 1982; Yamada, 1983; Hynes, 1985; Ruoslahti et al., 1988; Hynes, 1990; Owens et al., 1986). Structural diversity in FNs is brought about by alternative splicing of three regions (ED-A, ED-B and IIICS) of the primary FN transcript (Hynes, 1985; Zardi et al., 1987) to generate at least 20 different isoforms, some of which are differentially expressed in tumour and normal tissue. As well as being regulated in a tissue- and developmentally-specific manner, it is known that the splicing pattern of FN-pre-mRNA is deregulated in transformed cells and in malignancies (Castellani et al., 1986; Borsi et al, 1987; Vartio et al., 1987, Zardi et al, 1987; Barone et al, 1989; Carnemolla et al, 1989; Oyama et al, 1989, 1990; Borsi et al, 1992b). In fact, the FN isoforms containing the ED-A, ED-B and IIICS sequences are expressed to a greater extent in transformed and malignant tumour cells than in normal cells. In particular, the FN isoform containing the ED-B sequence (B+ isoform), is highly expressed in foetal and tumour tissues as well as during wound healing, but restricted in expression in normal adult tissues (Norton et al, 1987; Schwarzbauer et al, 1987; Gutman and Kornblihtt, 1987; Carnemolla et al, 1989; ffrench-Constant et al, 1989; ffrench-Constant and Hynes, 1989; Laitinen et al, 1991.) B+ FN molecules are undetectable in mature vessels, but upregulated in angiogenic blood vessels in normal (e.g. development of the endometrium), pathologic (e.g. in diabetic retinopathy) and tumour development (Castellani et al, 1994).

The ED-B sequence is a complete type III-homology repeat encoded by a single exon and comprising 91 amino acids. In contrast to the alternatively spliced IIICS isoform, which contains a cell type-specific binding site, the biological function of the A+ and B+ isoforms is still a matter of speculation (Humphries et al., 1986).

The presence of B+ isoform itself constitutes a tumour-induced neoantigen, but in addition, ED-B expression exposes a normally cryptic antigen within the type III repeat 7 (preceding ED-B); since this epitope is not exposed in FN molecules lacking ED-B, it follows that ED-B expression induces the expression of neoantigens both directly and indirectly. This cryptic antigenic site forms the target of a monoclonal antibody (mAb) named BC-1 (Carnemolla et al, 1992). The specificity and biological properties of this mAb have been described in EP 0 344 134 B1 and it is obtainable from the hybridoma deposited at the European Collection of Animal Cell Cultures, Porton Down, Salisbury, UK under the number 88042101. The mAb has been successfully used to localise the angiogenic blood vessels of tumours without crossreactivity to mature vascular endothelium, illustrating the potential of FN isoforms for vascular targeting using antibodies.

However, there remain certain caveats to the specificity of the BC-1 mAb. The fact that BC-1 does not directly recognize the B+ isoform has raised the question of whether in some tissues, the epitope recognized by BC-1 could be unmasked without the presence of ED-B and therefore lead indirectly to unwanted crossreactivity of BC-1. Furthermore, BC-1 is strictly specific for the human B+ isoform, meaning that studies in animals on the biodistribution and tumour localisation of BC-1 are not possible. Although polyclonal antibodies to recombinant fusion proteins containing the B+ isoform have been produced (Peters et al, 1995), they are only reactive with FN which has been treated with N-glycanase to unmask the epitope.

A further general problem with the use of mouse monoclonal antibodies is the human.anti-mouse antibody (HAMA) response (Schroff et al, 1985; Dejager et al, 1988). HAMA responses have a range of effects, from neutralisation of the administered antibody leading to a reduced therapeutic dose, through to allergic responses, serum sickness and renal impairment.

Although polyclonal antisera reactive with recombinant ED-B have been identified (see above), the isolation of mAbs with the same specificity as BC-1 following immunisation of mice has generally proved difficult because human and mouse ED-B proteins show virtually 100% sequence homology. The human protein may therefore look like a self-antigen to the mouse which then does not mount an immune response to it. In fact, in over ten years of intensive research in this field, only a single mAb has been identified with indirect reactivity to the B+ FN isoform (BC-1), with none recognising ED-B directly. It is almost certainly significant that the specificity of BC-1 is for a cryptic epitope exposed as a consequence of ED-B, rather than for part of ED-B itself, which is likely to be absent from mouse FN and therefore not seen as "self" by the immune system of the mouse.

Realisation of the present invention has been achieved using an alternative strategy to those previously used and where prior immunisation with fibronectin or ED-B is not required: antibodies with specificity for the ED-β isoform have been obtained as single chain Fvs (scfvs) from libraries of human antibody variable regions displayed on the surface of filamentous bacteriophage (Nissim et al., 1994; see also WO92/01047, WO92/20791, WO93/06213, WO93/11236, WO93/19172).

We have found using an antibody phage library that specific scFvs can be isolated both by direct selection on recombinant FN-fragments containing the ED-B domain and on recombinant ED-B itself when these antigens are coated onto a solid surface ("panning"). These same sources of antigen have also been successfully used to produce "second generation" scFvs with improved properties relative to the parent clones in a process of "affinity maturation". We have found that the isolated scFvs react strongly and specifically with the B+ isoform of human FN without prior treatment with N-glycanase.

In anti-tumour applications the human antibody antigen binding domains provided by the present invention have the advantage of not being subject to the HAMA response. Furthermore, as exemplified herein, they are useful in immunohistochemical analysis of tumour tissue, both in vitro and in vivo. These and other uses are discussed further herein and are apparent to the person of ordinary skill in the art.

TERMINOLOGY

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate.

Antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al., 1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, 1988; Huston et al, 1988) (viii) bispecific single chain Fv dimers (PCT/US92/09965) and (ix) "diabodies", multivalent or multispecific fragments constructed by gene fusion (WO94/13804; Holliger et al, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger and Winter, 1993), eg prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, (1991).

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. Preferably, an antigen binding domain comprises an antibody light chain variable region (VL) and an antibody heavy chain variable region (VH).

Specific

This refers to the situation in which one member of a specific binding pair will not show any significant binding to molecules other than its specific binding partner. The term is also applicable where eg an antigen binding domain is specific for a particular epitope which is carried by a number of antigens, in which case the specific binding member carrying the antigen binding domain will be able to bind to the various antigens carrying the epitope.

Functionally Equivalent Variant Form

This refers to a molecule (the variant) which although having structural differences to another molecule (the parent) retains some significant homology and also at least some of the biological function of the parent molecule, e.g. the ability to bind a particular antigen or epitope. Variants may be in the form of fragments, derivatives or mutants. A variant, derivative or mutant may be obtained by modification of the parent molecule by the addition, deletion, substitution or insertion of one or more amino acids, or by the linkage of another molecule. These changes may be made at the nucleotide or protein level. For example, the encoded polypeptide may be a Fab fragment which is then linked to an Fc tail from another source. Alternatively, a marker such as an enzyme, flourescein, etc, may be linked.

SUMMARY OF THE PRESENT INVENTION

According to the present invention there is provided a specific binding member which is specific for the ED-B oncofoetal domain of fibronectin (FN).

Specific binding members according to the invention bind the ED-B domain directly. In one embodiment, a specific binding member binds, after treatment of the FN with the protease thermolysin, to a, any or all FN containing ED-B. In a further embodiment a specific binding member binds to a, any or all FN containing type III homology repeats which include the ED-B domain. Known FNs are identified in two papers by Carnemolla et al., 1989; 1992). Reference to "all FNs containing ED-B" may be taken as reference to all FNs identified in those papers as containing ED-B.

The specific binding member preferably binds human ED-B, and preferably B+FN of at least one other species, such as mouse, rat and/or chicken. Preferably, the specific binding pair member is able to bind both human fibronectin ED-B and a non-human fibronectin ED-B, such as that of a mouse, allowing for testing and analysis of the sbp member in an animal model.

Specific binding pair members according to the present invention bind fibronectin ED-B without competing with the publicly available deposited antibody BC-1 discussed elsewhere herein. BC-1 is strictly specific for human B+ isoform. Specific binding pair members according to the present invention do not bind the same epitope as BC-1.

Binding of a specific binding member according to the present invention to B+FN may be inhibited by the ED-B domain.

In an aspect of the present invention the binding domain has, when measured as a purified monomer, a dissociation constant (Kd) of $6 \times 10^{-8}$ M or less for ED-B FN.

In an aspect of the present invention the binding domain is reactive with, i.e. able to bind, fibronectin ED-B without prior treatment of the fibronectin ED-B with N-glycanase.

Specific binding pair members according to the present invention may be provided as isolates or in purified form, that is to say in a preparation or formulation free of other specific binding pair members, e.g. antibodies or antibody fragments, or free of other specific binding pair members able to bind fibronectin ED-B. Preferably, the specific binding members according to the present invention are provided in substantially pure form. They may be "monoclonal" in the sense of being from a single clone, rather than being restricted to antibodies obtained using traditional hybridoma technology. As discussed, specific binding pair members according to the present invention may be obtained using bacteriophage display technology and/or expression in recombinant, e.g. bacterial, host cells. There is no prior disclosure of a monoclonal specific binding pair member which directly binds fibronectin ED-B.

Preferably, the specific binding member comprises an antibody. The specific binding member may comprise a polypeptide sequence in the form of an antibody fragment such as single chain Fv (scFv). Other types of antibody fragments may also be utilised such as Fab, Fab', F(ab')2, Fabc, Facb or a diabody (Winter and Milstein, 1991; WO94/13804). The specific binding member may be in the form of a whole antibody. The whole antibody may be in any of the forms of the antibody isotypes eg IgG, IgA, IgD, IgE and IgM and any of the forms of the isotype subclasses eg IgG1 or IgG4.

The antibody may be of any origin, for example, human, murine, ovine or lapine. Other derivations will be clear to those of skill in the art. Preferably, the antibody is of human origin. By "human" is meant an antibody that is partly or entirely derived from a human cDNA, protein or peptide library. This term includes humanized peptides and proteins of non-human origin that have been modified in order to impart human characteristics to the antibody molecule and so allow the molecule to bypass the defences of the human immune system.

The specific binding member may also be in the form of an engineered antibody e.g. a bispecific antibody molecule (or a fragment such as F(ab')2) which has one antigen binding arm (i.e. specific domain) against fibronectin ED-B as disclosed and another arm against a different specificity, or a bivalent or multivalent molecule.

In addition to antibody sequences, the specific binding member may comprise other amino acids, e.g. forming a peptide or polypeptide, or to impart to the molecule another functional characteristic in addition to ability to bind antigen. For example, the specific binding member may comprise a label, an enzyme or a fragment thereof and so on.

The binding domain may comprise part or all of a VH domain encoded by a germ line segment or a re-arranged gene segment. The binding domain may comprise part or all of a VL kappa domain or a VL lambda domain.

The binding domain may comprise a VH1, VH3 or VH4 germ-line gene sequence, or a re-arranged form thereof.

A specific binding member according to the present invention may comprise a heavy chain variable region ("VH" domain) derived from human germline DP47, the sequence of which is shown in FIG. 1(a), residues 1 to 98. The 'DP' nomenclature is described in Tomlinson et al, (1992). The amino acid sequence of the CDR3 may be Ser Leu Pro Lys (SEQ ID NO: 12). The amino acid sequence of the CDR3 may be Gly Val Gly Ala Phe Arg Pro Tyr Arg Lys His Glu (SEQ ID NO: 1). Thus, the binding domain of a specific binding member according to the present invention may include a VH domain that comprises the amino acid sequences shown in FIG. 1(a) for CGS1 and CGS2.

The binding domain may comprise a light chain variable region ("VL" domain) derived from human germline DPL16, the sequence of which is shown in FIG. 1(b) as codons 1-90.

The VL domain may comprise a CDR3 sequence Asn Ser Ser Pro Val Val Leu Asn Gly Val Val (SEQ ID NO: 2). The VL domain may comprise a CDR 3 sequence Asn Ser Ser Pro Phe Glu His Asn Leu Val Val (SEQ ID NO: 3).

Specific binding members of the invention may comprise functionally equivalent variants of the sequences shown in FIG. 1, e.g. one or more amino acids has been inserted, deleted, substituted or added, provided a property as set out herein is retained. For instance, the CDR3 sequence may be altered, or one or more changes may be made to the framework regions, or the framework may be replaced with another framework region or a modified form, provided the specific binding member binds ED-B.

One or more CDR's from a VL or VH domain of an antigen binding domain of an antibody disclosed herein may be used in so-called "CDR-grafting" in which one or more CDR sequences of a first antibody is placed within a framework of sequences not of that antibody, e.g. of another antibody, as disclosed in EP-B-0239400. CDR sequences for CGS1 and CGS2 are shown in FIGS. 1(a) and 1(b).

A specific binding member according to the invention may be one which competes with an antibody or scFv described herein for binding to fibronectin ED-B. Competition between binding members may be assayed easily in vitro, for example by tagging a specific reporter molecule to one binding member which can be detected in the presence of other untagged binding member(s), to enable identification of specific binding members which bind the same epitope or an overlapping epitope.

A specific binding member according to the present invention may be used in a method comprising causing or allowing binding of the specific binding member to its epitope. Binding may follow administration of the specific binding member to a mammal, e.g. human or rodent such as mouse.

The present invention provides the use of a specific binding member as above to use as a diagnostic reagent for tumours. Animal model experimental evidence described below shows that binding members according to the present invention are useful in in vivo tumour localisation.

Preferred specific binding members according to the present invention include those which bind to human tumours, e.g. in a cryostat section, which show an invasive and angiogenic phenotype and those which bind to embryonic tissues, e.g. in a cryostat section. Binding may be demonstrated by immunocytochemical staining.

In a preferred embodiment, the specific binding member does not bind, or does not bind significantly, tenascin, an extracellular matrix protein.

In another preferred embodiment, the specific binding member does not bind, or does not bind significantly, normal human skin, e.g. in a cryostat section and/or as demonstrated using immunocytochemical staining.

Further embodiments of specific binding members according to the present invention do not bind, or do not bind significantly, to one or more normal tissues (e.g. in cryostat section and/or as demonstrated using immunocytochemical staining) selected from liver, spleen, kidney, stomach, small intestine, large intestine, ovary, uterus, bladder, pancreas, suprarenal glands, skeletal muscle, heart, lung, thyroid and brain.

A specific binding member for ED-B may be used as an in vivo targeting agent which may be used to specifically demonstrate the presence and location of tumours expressing or associated with fibronectin ED-B. It may be used as an imaging agent. The present invention provides a method of determining the presence of a cell or tumour expressing or associated with fibronectin ED-B expression, the method comprising contacting cells with a specific binding member as provided and determining the binding of the specific binding member to the cells. The method may be performed in vivo, or in vitro on a test sample of cells removed from the body.

The reactivities of antibodies on a cell sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, eg via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

The signals generated by individual antibody-reporter conjugates may be used to derive quantifiable absolute or relative data of the relevant antibody binding in cell samples (normal and test). In addition, a general nuclear stain such as propidium iodide may be used to enumerate the total cell population in a sample, allowing the provision of quantitative ratios of individual cell populations relative to the total cells. When a radionucleotide such as $^{125}$I, $^{111}$In or $^{99m}$Tc is attached to an antibody, if that antibody localises preferentially in tumour rather than normal tissues, the presence of radiolabel in tumour tissue can be detected and quantitated using a gamma camera. The quality of the tumour image obtained is directly correlated to the signal:noise ratio.

The antibodies may be utilised as diagnostic agents to trace newly vascularised tumours, and may also be employed, e.g. in modified form, to deliver cytotoxic agents or to trigger coagulation within new blood vessels, thus starving the developing tumour of oxygen and nutrients and constituting an indirect form of tumour therapy.

The present invention also provides for the use of a specific binding member as above to use as a therapeutic reagent, for example when coupled, bound or engineered as a fusion protein to possess an effector function. A specific binding member according to the present invention may be used to target a toxin, radioactivity, T-cells, killer cells or other molecules to a tumour expressing or associated with the antigen of interest.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Appropriate doses of antibody are well known in the art; see Ledermann et al., (1991); Bagshawe K. D. et al. (1991).

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A specific binding member according to the present invention may be made by expression from encoding nucleic acid. Nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid.

The nucleic acid may encode any of the amino acid sequences of the antibody antigen binding domains described herein or any functionally equivalent form. Changes may be made at the nucleotide level by addition, substitution, deletion or insertion of one or more nucleotides, which changes may or may not be reflected at the amino acid level, dependent on the degeneracy of the genetic code.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is E. coli.

The expression of antibodies and antibody fragments in prokaryotic cells such as E. coli is well established in the art. For a review, see for example Plückthun, (1991). Expression in eukaryotic cells in culture is also available to those skilled in the art as an option for production of a specific binding member, see for recent reviews, for example Reff, (1993); Trill et al. (1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

Following production of a specific binding member it may be used for example in any of the manners disclosed herein, such as in the formulation of a pharmaceutical or a diagnostic product, such as a kit comprising in addition to the specific binding member one or more reagents for determining binding of the member to cells, as discussed.

Further aspects of the invention and embodiments will be apparent to those skilled in the art. In order that the present invention is fully understood, the following examples are provided by way of exemplification only and not by way of limitation. Reference is made to the following figures:

FIG. 1 shows aligned amino acid sequences of the VH and VL of scFvs CGS-1 and CGS-2. FIG. 1(*a*) shows VH sequences; FIG. 1(*b*) shows VL sequences. CDRs (1, 2 and 3) are indicated. The most homologous human germline VH to both scFvs is the DP47 segment of the VH3 family; the VL segment of both clones is DPL16, the light chain used to build the original scFv library (Nissim et al, 1994). Residues that distinguish the two clones from each other are underlined.

Figure 2B:
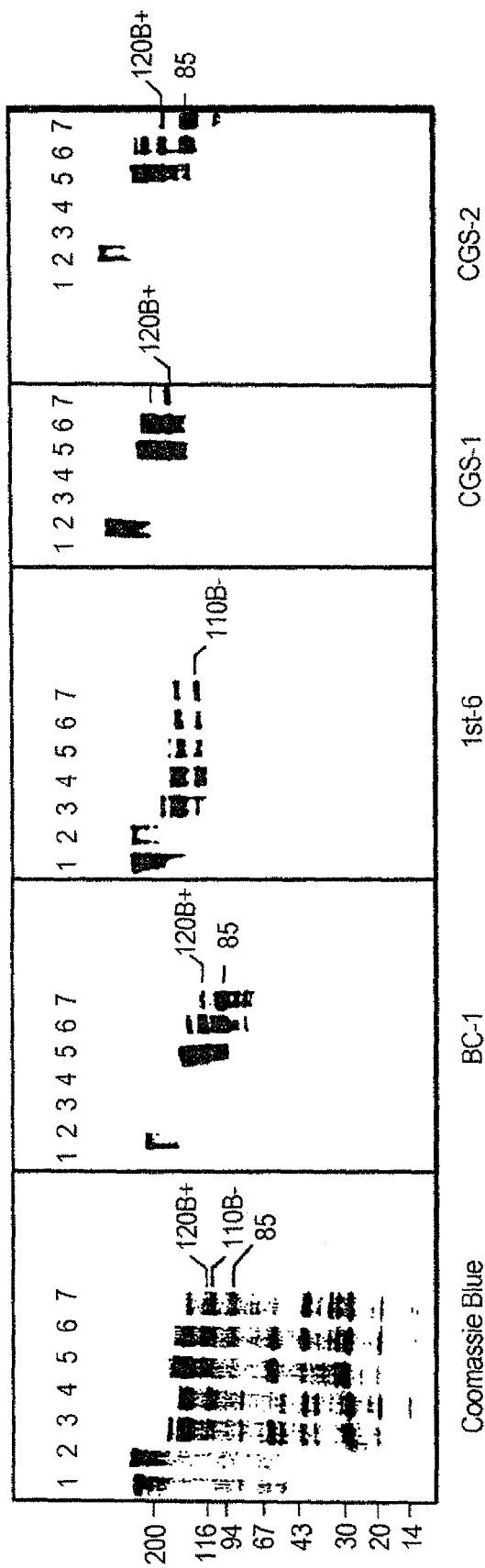

FIG. 2: FIG. 2A shows a model of the domain structure of a human FN subunit. The IIICS, ED-A and ED-B regions of variability, due to alternative splicing of the FN pre-mRNA, are indicated. The figure also indicates the internal homologies as well as the main thermolysin digestion products containing ED-B (Zardi et al, 1987). FIG. 2B shows 4-18% SDS-PAGE of plasma and WI38VA FN and their thermolysin digests stained with Coomassie Blue and immunoblots probed with BC-1, IST-6, CGS-1 and CGS-2. Undigested (lane 1) and digested plasma FN using thermolysin at 1 µg/mg of FN (lane 3) and 10 µg/mg of FN (lane 4). Undigested (lane 2) and digested WI38VA FN using thermolysin at 1 µg/mg (lane 5), 5 µg/mg (lane 6) and 10 µg/mg (lane 7) of FN. The numbers on the right hand side indicate the main thermolysin digestion products shown in FIG. 2A. The values on the left indicate the molecular weight standards in kiloDalton (kD).

Figure 3B:
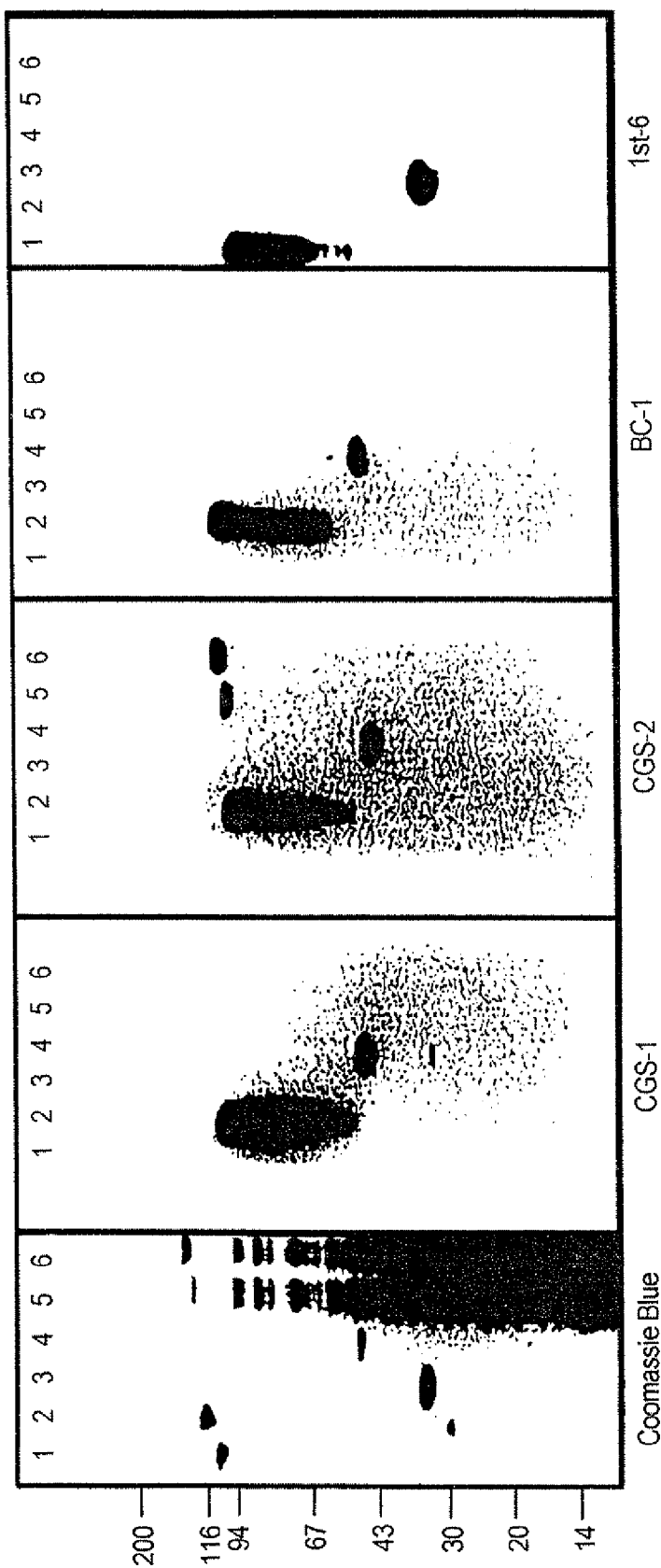

FIG. 3: FIG. 3A shows the FN type III repeat sequences contained in the fusion and recombinant proteins expressed in *E. coli* and the reactivity of these proteins with CGS-1 and CGS-2 and with the mAbs BC-1 and IST-6. FIG. 3B shows a Coomassie Blue stained gel and alongside the immunoblots probed with CGS-1, CGS-2, BC-1, IST-6. The numbering of the lanes corresponds to that of the peptide constructs in the upper part of the figure. The values on the left indicate the molecular weight standards in kD.

Figure 4:
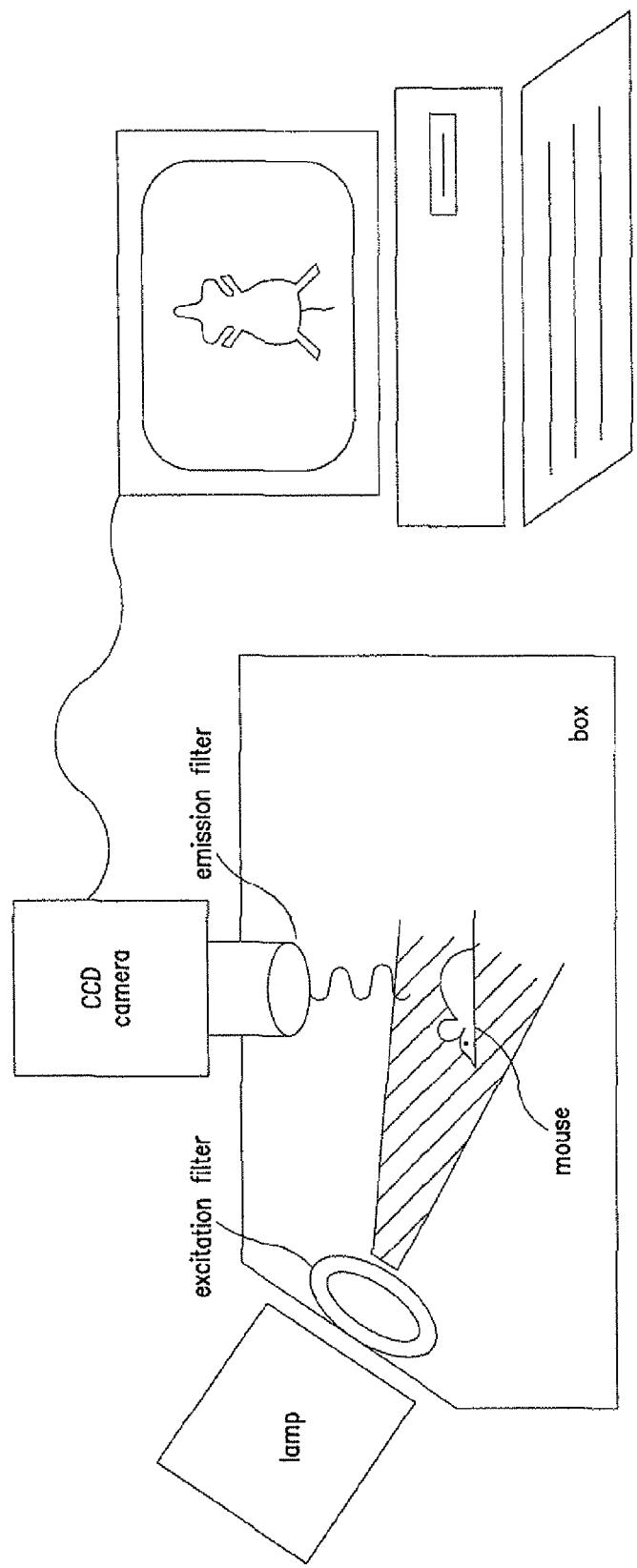

FIG. 4: Infrared Mouse Imager; the mouse imager used for the targeting experiments consists of a black, non-fluorescent box equipped with a tungsten halogen lamp, excitation and emission filters specific for the CY7 infrared fluorophore and a computer-controlled 8-bit monochrome CCD-camera.

Figure 5:
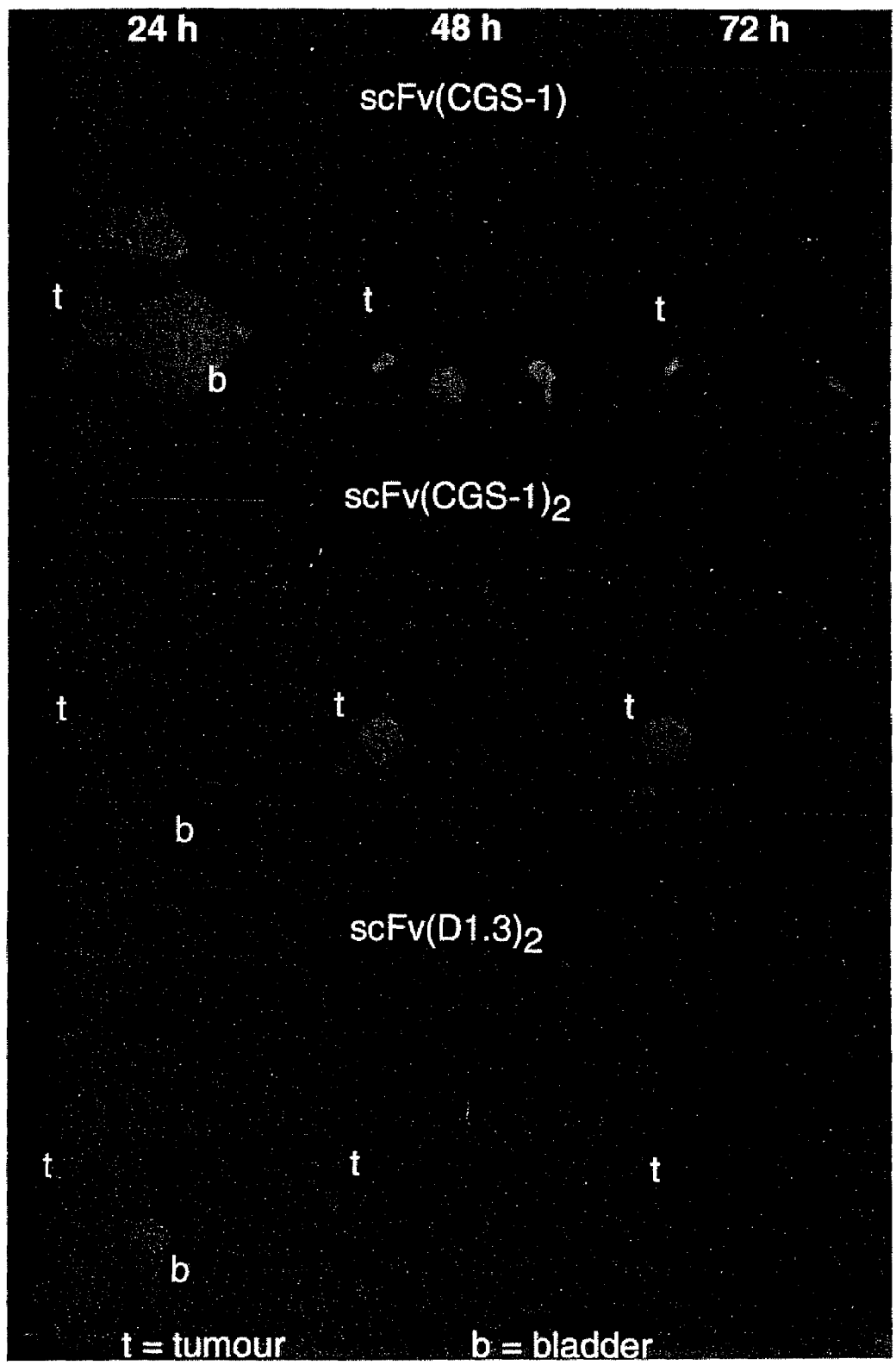

FIG. 5: Targeting of fluorescently labelled antibody fragments to the F9 murine teratocarcinoma using the monomeric scFv(CGS-1) and dimeric scFv(CGS-1)$_2$ directed to B–FN. The dimeric scFv(D1.3)$_2$ with a binding specificity to lysozyme was used as a negative control.

Figure 6:
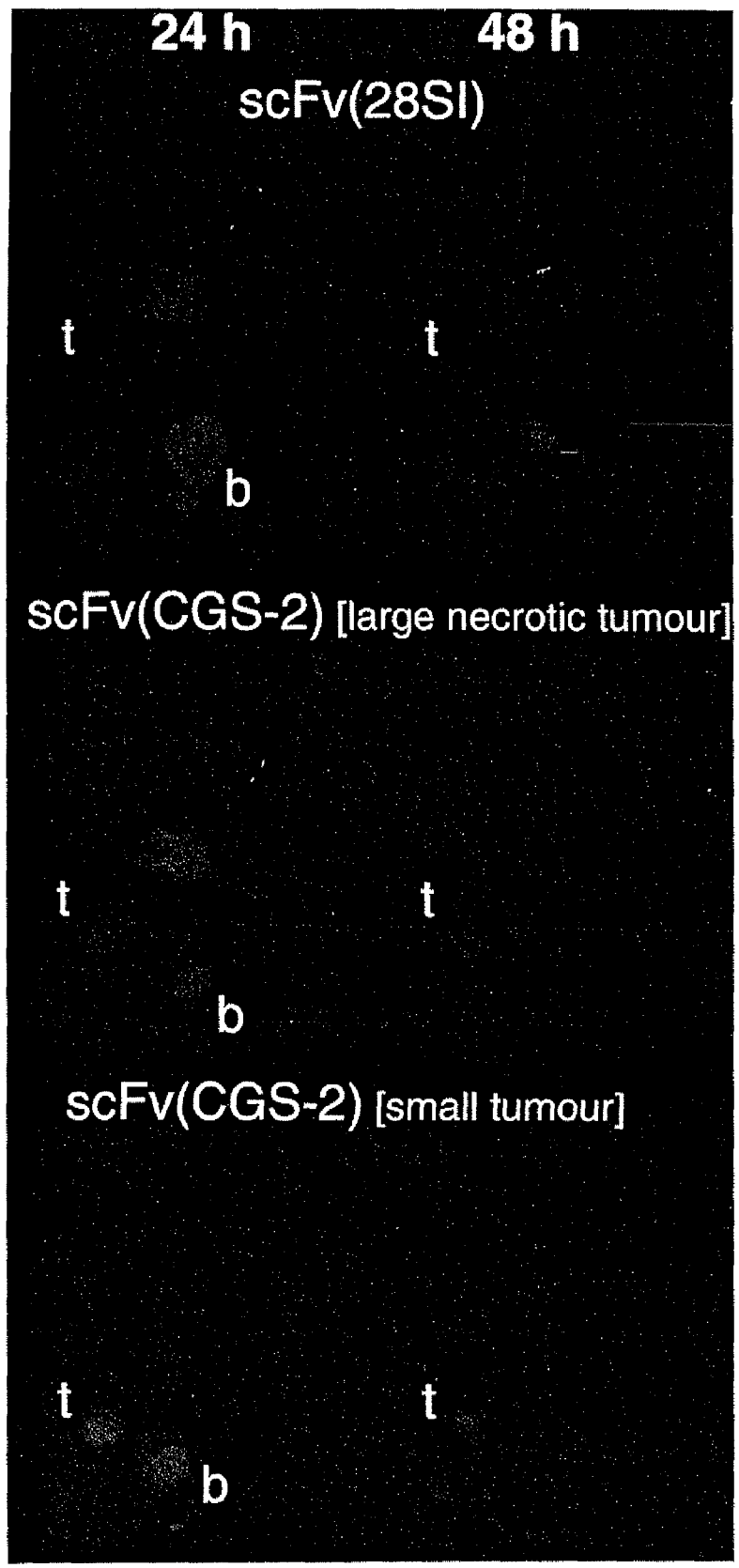

FIG. 6: Targeting of fluorescently labelled antibody fragments to the F9 murine teratocarcinoma using the affinity matured scFv(CGS-2) and the lower affinity scFv(28SI) directed to the same epitope of B–FN. Targeting is detected both in a large tumours (approx. 0.6 grams), covered at 48 h by a black crust that partially obscures the imaging, and in small tumours (approx. 0.2 grams).

All documents mentioned herein are incorporated by reference.

LIST OF EXAMPLES

Example 1—Isolation of human scFvs specific for the ED-B domain of human FN.

Example 2—Affinity maturation of human scFvs specific for the ED-B domain of human FN.

Example 3—Specificity of affinity matured scFvs for ED-B-containing fibronectins.

Example 4—The use of affinity matured anti-ED-B scFvs in immunocytochemical staining of human and mouse tumour sections.

Example 5—The use of affinity matured anti-ED-B scFvs in in vivo targeting of human tumours.

Example 6—Targeting of xenografted murine F9 teratocarcinoma in nude mice.

Example 1

Isolation of Human scFvs Specific for the Ed-B Domain of Human FN

A human scFv phage library (Nissim et al, 1994) was used for the selection of recombinant antibodies. Two different forms of the ED-β isoform were used as a source of antigen for selection and in both cases, the isoform was recombinant human protein.

Recombinant FN peptides containing the type III repeats 2-11 (B−) and 2-11 (B+) were expressed in *Esherichia coli*.

A construct was made using FN cDNA from the clones pFH154 (Kornblihtt et al 1985), λF10 and λF2 (Carnemolla et al, 1989). The cDNA constructs, spanning bases 2229-4787, (Kornblihtt et al, 1985) were inserted into the vector pQE-3/5 using the QIAexpress kit from Qiagen (Chatsworth, Calif.). The recombinants FN-III 2-11 (B−) and (B+) were purified by immunoaffinity chromatography using the mAb 3E3 (Pierschbacher et al 1981) conjugated to Sepharose 4B (Pharmacia). DNA fragments for the preparation of the recombinant FN fragments containing the type III homology repeats 7B89, 789, ED-B and FN-6 were produced by polymerase chain reaction (PCR) amplification using UltMa DNA polymerase (Perkin Elmer), using cDNA from clones FN 2-11 (B+) and FN 2-11 (B−) as template. Primers were designed to allow cloning of PCR products into pQE-12 using the QIAexpress kit (Qiagen). They were subsequently transformed into *E. coli* and expressed. All cDNA clones were sequenced using a Sequenase 2.0 DNA sequencing kit (USB).

Recombinant proteins were purified by Ni—NTA chromatography (IMAC), according to the manufacturers' instructions (Qiagen), using the hexahistidine tag (SEQ ID NO: 15) at the carboxy terminus of the FN fragments. The ED-B—βGal fusion protein was prepared by cloning ED-B cDNA into the λgt11 bacteriophage vector, to give clone λED-B. Clone λchFN60 (containing part of the ED-B sequence) was derived as a fusion protein from the cloned chicken FN pchFN60 (Norton et al, 1987).

For the selection of the human scFv phage library, three rounds of panning were performed for each of the two different recombinant antigens (7B89 and ED-B). The antigens were both coated onto immunotubes (Nunc; Maxisorp, Roskilde, Denmark) overnight at 50 µg/ml in PBS (20 mM phosphate buffer, 0.15M NaCl, pH 7.2). The first antigen was the recombinant FN fragment 7B89, in which the ED-B domain is flanked by the adjacent type III FM homology repeats; this was coated at 4° C. overnight. The second antigen used was recombinant ED-B (Zardi et al, 1987) with a carboxy terminal hexahistidine tag (SEQ ID NO: 15); this protein does not contain lysine residues, so that the terminal amino group of the first amino acid is available for site-specific covalent immobilisation of ED-B to reactive ELISA plates (Nunc; Covalink). Coating was carried out overnight at room temperature.

After three rounds of panning, the eluted phage were infected into HB2151 *E. coli* cells and plated as described (Nissim et al., 1994). After each round of selection, 95 ampicillin-resistant single colonies were screened to identify antigen-specific scFvs by ELISA. Clones which gave the highest ELISA signals on the antigens used for panning were selected for further analysis and for affinity maturation. These clones were also demonstrated to give specific staining of sections of glioblastoma multiforme and breast tumours by immunocytochemical staining, described in more detail in Example 4.

Example 2

Affinity Maturation of Human scFvs Specific for the ED-B Domain of Human FN

Clones 35GE (from selection with 7B89) and 28SI (from selection with the ED-B domain alone) were selected as candidate antibodies for affinity maturation. In order to diversify the light chains as a means of improving affinity, we then explored a simple affinity maturation strategy based on randomizing the central six residues (DSSGNH (SEQ ID NO: 6)) of the light chain CDR3 using degenerate oligonucleotides and PCR (FIG. 1), providing a potential sequence diversity of $20^6 = 6.4 \times 10^7$. This region (along with the heavy chain CDR3) is located at the centre of the antigen binding site (Padlan, 1994). We also mutated the arginine residue directly preceding the six residue stretch to serine, in order to avoid the possibility of electrostatic effects dominating the selection.

Plasmid from a single bacterial colony expressing the "parent" scFv fragment was PCR amplified with primers LMB3 (5' CAG GAA ACA GCT ATG AC 3' (SEQ ID NO: 7)) and CDR3-6-VL-FOR (5' CTT GGT CCC TCC GCC GAA TAC CAC MNN MNN MNN MNN MNN AGA GGA GTT ACA GTA ATA GTC AGC CTC 3' (SEQ ID NO: 4)) (94 C [1']-55 C [1']-72 C [1'30"]25 cycles; see Marks et al., 1991, for buffers and conditions). The resulting product was gel-purified (in order to remove traces of the plasmid containing the original scFv gene) and used as template for a second amplification step with primers LMB3 and J1-Not-FOR (5' ATT GCT TTT CCT TTT TGC GGC CGC GCC TAG GAC GGT CAG CTT GGT CCC TCC GCC 3' (SEQ ID NO: 5)) (94 C [1']-55C [1']-72 C [1'30"], 25 cycles). The crude PCR product, which ran as a single band of the correct molecular weight on agarose gel, was directly purified from the PCR mixture using Spin-Bind (FMC, Rockland, Me., USA), double-digested with Nco1/Not1 and ligated into gel-purified Nco1/Not1-digested phagemid pHEN1 (Hoogenboom et al., 1991) containing a dummy Nco1/Not1 insert to facilitate the separation of double-digested from single-digested vector. The vector was prepared with a Qiagen (Chatsworth, Calif., U.S.A.) plasmid maxi-prep kit. Approximately 5 µg of digested plasmid and of insert were used in the ligation mix, which was extracted once with phenol, once with phenol/choroform/isoamyl alcohol (25:25:1), then ethanol-precipitated using glycogen (Boehringer, Mannheim, Germany) as a carrier and speed-vac dried. The pellet was resuspended in 20 µl water and electroporated in electrocompetent TG1 *E. coli* cells (Gibson, 1984). We typically used electrocompetent cells with a titre of $10^9$ transformants/µg if glycerol stocks are used, or $10^{10}$ transformants/µg with freshly-prepared electrocompetent cells. This yielded typically >$10^7$ clones with the procedure outlined here.

The maturation library was then processed as for the Nissim library (Nissim et al., 1994) to produce phage particles, which were used for one round of selection on immunotubes using 7B89 (10 µg/ml) as antigen, followed by a round of kinetic selection (Hawkins et al., 1992). This selection step was performed by incubating biotinylated 7B89 (10 nM) with the phage suspension (approx. $10^{12}$ t.u.) in 2% milk-PBS (2% MPBS) from the first round of selection for 5 minutes, then adding non-biotinylated 7B89 (1 µM) and letting the competition proceed for 30 minutes. 100 µl of streptavidin-coated dynabeads (Dynal; M480) preblocked in 2% MPBS were then added to the reaction mixture, mixed for 2 minutes and then captured on a magnet and washed 10 times with alternate washes of (PBS+0.1% Tween-20) and PBS. Phage were eluted from the beads with 0.5 ml 100 mM triethylamine. This solution was then neutralized with 0.25 ml 1 M Tris, pH 7.4, and used to infect exponentially growing HB2151 cells (Nissim et al., 1994). 95 ampicillin-resistant single colonies were used to produce scFv-containing supernatants (Nissim et al., 1994) which were screened by ELISA, immunohistochemistry and BIAcore to identify the best binders. They were then subcloned between Sfi1/Not1 sites of the pDN268 expression vector (Neri et al., 1996), which appends a phosphorylatable tag, the FLAG epitope and a hexahistidine tag (SEQ ID NO: 15) at the C-terminal extremity of the scFv.

Single colonies of the relevant antibodies subcloned in pDN268 were grown at 37° C. in 2×TY containing 100 mg/l ampicillin and 0.1% glucose. When the cell culture reached $OD^{600}=0.8$, IPTG was added to a final concentration of 1 mM and growth continued for 16-20 hrs at 30° C. After centrifugation (GS-3 Sorvall rotor, 7000 rpm, 30 minutes), the supernatant was filtered, concentrated and exchanged into loading buffer (50 mM phosphate, pH 7.4 500 mM NaCl, 20 mM imidazole) using a Minisette (Filtron) tangential flow apparatus. The resulting solution was loaded onto 1 ml Ni-NTA resin (Qiagen), washed with 50 ml loading buffer and eluted with elution buffer (50 mM phosphate, pH 7.4, 500 mM NaCl, 100 mM imidazole). The purified antibody was analysed by SDS-PAGE (Laemmli, 1970) and dialysed versus PBS at 4° C. Purified scFv preparations were further processed by gel-filtration using an FPLC apparatus equipped with a S-75 column (Pharmacia), since it is known that multivalent scFv fragments may exhibit an artificially good binding on BIAcore (Jonsson et al., 1991) by virtue of avidity effects (Nissim et al., 1994; Crothers and Metzger, 1972). The antibody concentration of FPLC-purified monomeric fractions was determined spectrophotometrically assuming an absorbance at 280 nm of 1.4 units for a 1 mg/ml scFv solution.

et al., 1992; Low et al., 1996), and yields antibodies with similar affinities as those derived from very large phage antibody libraries (Griffiths et al., 1994; Vaughan et al., 1996).

The affinity matured clones CGS-1 and CGS-2 were sequenced and aligned to a database of human germline antibody V genes (V-BASE) then translated using MacVector software. The VH gene of both clones was most homologous to human germline DP47 (VH3), and in addition each clone had a different VH CDR3 sequence (FIG. 1). The VL gene of both clones was the DPL16 germline used in the construction of the human synthetic scFv repertoire described in Nissim et al, 1994. The VL CDR3 sequences differed from each other at four out of six of the randomised residues (FIG. 1b).

TABLE I

Kinetic and dissociation constants of monomeric scFv fragments
CGS-1 and CGS-2 towards ED-B domain-containing proteins

| | Antigen: | | | | | | | | |
|---|---|---|---|---|---|---|---|---|---|
| | ED-B | | | 7B89 | | | FN WI38VA | | |
| ScFv: | CGS-1 | SI28 | CGS-2 | CGS-1 | SI28 | CGS-2 | CGS-1 | SI28 | CGS-2 |
| $k_{off}(s^{-1})*$ | $7.0 \times 10^{-3}$ | $2.7 \times 10^{-2}$ | $1.5 \times 10^{-4}$ | $3.9 \times 10^{-3}$ | $3.0 \times 10^{-2}$ | $2.3 \times 10^{-4}$ | $5.0 \times 10^{-3}$ | $7.1 \times 10^{-2}$ | $6.5 \times 10^{-4}$ |
| $k_{on}(M^{-1}s^{-1})*$ | $1.3 \times 10^{5}$ | $2.5 \times 10^{5}$ | $1.3 \times 10^{5}$ | $1.1 \times 10^{5}$ | $2.9 \times 10^{5}$ | $1.1 \times 10^{5}$ | $4.1 \times 10^{5}$ | $1.2 \times 10^{6}$ | $2.9 \times 10^{5}$ |
| $k_d(M)*$ | $5.4 \times 10^{-8}$ | $1.1 \times 10^{-7}$ | $1.1 \times 10^{-9}$ | $3.5 \times 10^{-8}$ | $1.0 \times 10^{-7}$ | $2.1 \times 10^{-9}$ | $1.2 \times 10^{-8}$ | $5.9 \times 10^{-8}$ | $2.4 \times 10^{-9}$ |

Legend to Table I
Experiments were performed as described in the Materials and Methods section.
*The $k_{off}$ and $k_{on}$ values are accurate to +/−30%, on the basis of the precision of concentration determinations and in relation to the slightly different results obtained when different regions of the sensograms are used for the fitting procedure. $K_d = k_{off}/k_{on}$.

Binding of monovalent scFv at various concentrations in the 0.1-1 μM range in PBS was measured on a BIAcore machine (Pharmacia Biosensor), using the following antigens: (i) 1000 Resonance Units (RU) of biotinylated recombinant FN fragment 7B89 immobilised on a streptavidin coated chip, which was bound specifically by 250 RU of scFv; (ii) 200 RU of recombinant ED-B, chemically immobilised at the N-terminal amino group, which was bound specifically by 600 RU of scFv; (iii) 3500 RU of ED-B-rich fibronectin WI38VA (see Example 3), which was bound specifically by 150 RU of scFv. Kinetic analysis of the data was performed according to the manufacturers' instructions. On the basis of qualitative BIAcore analysis of antibody-containing supernatants, one affinity-matured version of each scFv clone was selected: clone CGS-1 from selection with the 78B9 fragment and CGS-2 from selection with ED-B recombinant FN fragment. The association rate constants ($k_{on}$) and dissociation rate constants ($k_{off}$) are shown in Table 1, together with the calculated equilibrium dissociation constants (Kd) of both scFvs and the original clone 28SI. Although both the CGS-1 and CGS-2 clones have Kds in the nanomolar range, clone CGS-2 showed the best improvement over its parent clone, giving a Kd of in M (improved from 110 nM) with respect to all three proteins tested on the sensor chip (Table 1). The improvement was due mainly to a slower kinetic dissociation constant ($-10^{-4}$ s$^{-1}$), as measured with monomeric antibody preparations (not shown).

The maturation strategy appears to be general, and has yielded affinity improved antibodies against maltose binding protein, cytochrome C, the extracellular domain of murine endoglin (D. N., L. Wyder, R. Klemenz), cytomegalovirus (A. P., G. Neri, R. Botti, P. N.), the nuclear tumour marker HMGI-C protein (A. P., P. Soldani, V. Giancotti, P. N.) and the ovarian tumour marker placental alkaline phosphatase (M. Deonarain and A. A. Epenetos). The strategy therefore seems to be at least as effective as other maturation strategies (Marks Example 3

Specificity of Affinity Matured scFvs for ED-B-Containing Fibronectins

The immunoreactivity of the two affinity matured scFvs, CGS-1 and CGS-2, was assessed initially by ELISA and compared directly to the mAb BC-1 (which recognises the B−FN isoform) and mAb IST-6, which only recognises FN isoforms lacking ED-B (Carnemolla et al., 1989; 1992). The characterisation of these mAbs has been previously reported (Carnemolla et al, 1989; 1992). Fine specificity analysis was thereafter carried out using an extensive panel of FN fragments derived by thermolysin treatment and of recombinant fusion proteins.

The antigens used for ELISA and immunoblotting were prepared as follows. FN was purified from human plasma and from the conditioned medium of the WI38VA13 cell line as previously reported (Zardi et al, 1987). Purified FNs were digested with thermolysin (protease type X; Sigma Chemical Co.) as reported by Carnemolla et al (1989). Native FN 110 kD (B−) and native FN 120 kD (B+) fragments (see FIG. 2) were purified from a FN digest as previously reported (Borsi et al, 1991). The large isoform of tenascin-C was purified as reported by Saginati et al (1992). Recombinant proteins were expressed and purified as described in Example 1. SDS-PAGE and Western blotting were carried out as described by Carnemolla et al (1989).

All antigens used in ELISA were diluted in PBS to between 50-100 μg/ml and coated at 4° C. overnight onto Immuno-Plate wells (Nunc, Roskilde, Denmark). Unbound antigen was removed with PBS and plates were then blocked with PBS containing 3% (w/v) bovine serum albumin (BSA) for 2 h at 37° C. This was followed by four washes with PBS containing 0.05% Tween 20 (PBST). Antibodies were then allowed to bind at 37° C. for 1.5 h; scFvs were preincubated with an antiserum directed against the tag sequence: mAb M2 [Kodak, New Haven Conn.] for the FLAG tag or 9E10 [ATCC, Rockville, Md.] for the myc tag. Control antibodies tested were mAbs BC-1 and IST-6. After four washes with PBST, the plates were incubated for 1 h at 37° C. with 1:2000 diluted (in PBST+3% BSA) biotinylated goat anti-mouse IgG (Bio-SPA Division, Milan, Italy). The washes were repeated and Streptavidin-biotinylated alkaline phosphatase complex (Bio-SPA Division, Milan, Italy) was added (1:800 diluted in PBST containing 2 mM MgCl2) for 1 h at 37° C. The reaction was developed using Phosphatase substrate tablets (Sigma) in 10% diethanolamine, pH 9.8 and the optical density was read at 405 nm. The results are presented below in Table 2.

TABLE 2

|  | CGS-1 | CGS-2 | BC-1 | IST-6 |
|---|---|---|---|---|
| Plasma FN | 0.07 | 0.04 | 0.09 | 1.73 |
| WI38VA FN | 1.16 | 0.72 | 1.20 | 1.12 |
| n110 kD (B−) | 0.03 | 0.01 | 0.05 | 1.20 |
| n120 kD (B+) | 0.82 | 0.81 | 1.20 | 0.02 |
| rec FN7B89 | 1.11 | 1.02 | 1.02 | 0.01 |
| rec FN789 | 0.01 | 0.01 | 0.05 | 1.25 |
| rec ED-B | 1.21 | 1.32 | 0.15 | 0.04 |
| rec FN-6 | 0.01 | 0.01 | 0.08 | 0.03 |
| Tenascin | 0.01 | 0.02 | 0.06 | 0.02 |

Immunoreactivity of scFv and monoclonal antibodies with fibronectin-derived antigens measured by ELISA. The values represent the OD measured at 405 nm after subtraction of background signal. The data are the mean of four experiments showing a maximum 10% standard deviation.

The identity of the different forms of fibronectin used in the experiment is as follows: Plasma FN=human plasma fibronectin; WI38-VA FN=fibronectin from supernatants of SV40-transformed fibroblasts (Zardi et al, 1987); n110 kD=thermolysin treated FN domain 4, without ED-B; n120 kD=thermolysin treated FN domain 4, containing ED-B; rec FN7B89=ED-B domain flanked by adjacent type III FN homology repeats; rec FN789=type III FN homology repeats with an ED-B domain; rec ED-B=recombinant ED-B alone; rec FN6=recombinant FN domain 6.

Both CGS-1 and CGS-2 recognised the recombinant ED-B peptide, as well as all native or recombinant FN fragments containing the ED-B sequence, while they did not bind to any FN fragments lacking ED-B. Furthermore, CGS-1 and CGS-2 did not react with tenascin (which comprises fifteen type III homology repeats: Siri et al, 1991) and plasma FN, which does not contain detectable levels of the ED-B sequence in thermolysin digestion products (Zardi et al, 1987). In contrast, CGS-1 and CGS-2 reacted strongly with FN purified from the SV40-transformed cell line WI38VA. About 70-90% of FN molecules from this cell line contain ED-B, as shown by thermolysin digestion and S1 nuclease experiments using purified FN and total RNA prepared from the cell line (Zardi et al, 1987; Borsi et al, 1992). The specificity of the scFvs for the ED-B component of FN was demonstrated still further by using soluble recombinant ED-B to inhibit binding of CGS-1 and/or CGS-2 to FN on WI38VA cells (data not shown).

The data confirm that CGS-1 and CGS-2 only react specifically with FN derivatives that contain the ED-B domain. They both show the same reactivity as mAb BC-1, except in the case of recombinant ED-B, which was not recognised by BC-1. The intensity of the ELISA signals obtained relative to the mAb controls reflects the high specificity of the two scFvs for ED-B-containing antigens.

The specificity of CGS-1 and CGS-2 was investigated further on immunoblots using FN from plasma and WI38VA cells, and thermolysin digests thereof. Upon thermolysin digestion, FN from WI38VA cells (the majority of which contains ED-B) generates a 120 kD fragment (containing ED-B) and a minor 110 kD fragment which lacks ED-B (FIG. 2A; Zardi et al, 1987). Further digestion of the 120 kD domain generates two fragments: a 85 kD fragment which contains almost the entire ED-B sequence at its carboxy terminus, and a 35 kD sequence (FIG. 2A; Zardi et al, 1987).

On the left hand side of FIG. 2B is a Coomassie stained gel of the protein fractions analysed by immunoblotting. Plasma FN (lane 1) and thermolysin digests of the protein (lane 3, containing the 110 kD protein, and lane 4, containing digested 110 kD protein) were not recognised by CGS-1 and CGS-2. In contrast, ED-B-rich FN from WI38VA cells, both intact (lane 2) and after increasing thermolysin digestion (lanes 5, 6 and 7) was recognised by both scFv fragments. The smallest FN-derived fragment that could be recognised specifically by CGS-1 was the 120 kD protein (spanning type III repeats 2-11 inclusive), while CGS-2 was able to recognise the 85 kD fragment spanning repeats 2-7 in addition to the N-terminus of ED-B (FIG. 2B; Zardi et al, 1987). These results indicate that the two scFvs are reactive to distinct epitopes within the ED-B sequence. The binding of CGS-2 to the 85 kD domain indicates that the epitope for this clone lies in the amino terminus of ED-B. In contrast, the loss of CGS-1 binding when the 120 kD domain is digested to 85 kD demonstrates that it recognises an epitope located more toward the carboxy terminus of the ED-B molecule.

The fine specificity of CGS-1 and CGS-2 was investigated further by immunoblotting using recombinant FN fragments and fusion proteins with or without the ED-B sequence. The FN fusion proteins were prepared as described by Carnemolla et al (1989). The results of these experiments are shown in FIG. 3; for the association of the schematic diagram to the structure of the domains of human FN, see Carnemolla et al, 1992. The binding profiles obtained essentially confirmed what had previously been found by ELISA and immunoblots on purified FN and proteolytic cleavage products: CGS-1 and CGS-2 were strongly reactive with ED-B-containing FN fragments (lanes 2 and 4) but showed no reactivity to FN sequences lacking ED-B (lanes 1 and 3). CGS-1 did not react with either the human (lane 5) or the chicken (lane 6) ED-B fusion protein, while CGS-2 reacted strongly with both fragments (FIG. 3). This result may reflect certain conformational constraints of the epitope in ED-B-containing FN recognised by CGS-1; it is possible, for example, that the epitope is sensitive to denaturation or is not presented correctly when fractionated by SDS-PAGE and transferred to a solid support such as nitrocellulose.

Taken together, these results demonstrate that CGS-1 and CGS-2 bind strongly and specifically to ED-B-containing FNs, at regions distinct from one another and distinct from the ED-B structure which is recognised by the mAb BC-1.

Example 4

The Use of Affinity Matured Anti-Ed-B scFvs in Immunocytochemical Staining of Human and Mouse Tumours CGS-1 and CGS-2 have both been used to immunolocalise ED-B containing FN molecules in various normal and neoplastic human tissues. For normal tissue, skin was chosen, since the B–FN isoform is known to be expressed in macrophages and fibroblasts during cutaneous wound healing (Carnemolla et al, 1989; Brown et al, 1993). The two human tumours selected have previously been analysed for the specificity of staining with anti-fibronectin mAbs: glioblastoma multiforme has been studied in detail because endothelial cells in the vessels of this tumour are in a highly proliferative state with increased angiogenetic processes including the expression of B–FN isoforms (Castellani et al, 1994). Furthermore, studies using a diverse panel of normal, hyperplastic and neoplastic human breast tissues have provided further evidence of a correlation between angiogenesis and B–FN expression (Kaczmarek et al, 1994).

For the experiments described here, the immunohistochemical staining of CGS-1 and CGS-2 has been compared to that of mAb BC-1 (which recognises the B–FN isoform) and other mAbs known to react either to all known FN isoform variants (IST-4) or only to FN isoforms lacking ED-B (IST-6). The characterisation of all of these control antibodies has been previously reported (Carnemolla et al, 1989; 1992).

Normal and neoplastic tissues were obtained from samples taken during surgery. It has already been established that the preparation and fixation of tissues is critical for accurate and sensitive detection of FN-containing molecules (Castellani et al, 1994). For immunohistochemistry, 5 µm thick cryostat sections were air dried and fixed in cold acetone for ten minutes. Immunostaining was performed using a streptavidin-biotin alkaline phosphatase complex staining kit (Bio-SPA Division, Milan, Italy) and naphthol-AS-MX-phosphate and Fast Red TR (Sigma). Gill's haematoxylin was used as a counterstain, followed by mounting in glycergel (Dako, Carpenteria, Calif.) as reported previously by Castellani et al, 1994. In order to analyse specificity further in experiments where positive staining of tissues was obtained, specificity for ED-B was demonstrated by preincubation of antibodies with the recombinant ED-B domain, followed by detection as previously described.

The results of these experiments overall showed that both CGS-1 and CGS-2 reacted with the same histological structures as mAb BC-1. The staining pattern obtained with skin using CGS-1, CGS-2 and BC-1 reflects the absence of ED-B from the FN expressed in the dermis. In the staining of invasive ductal carcinoma sections, CGS-1, CGS-2 and BC-1 showed a restricted distribution of staining, confined to the border between the neoplastic cells and the stroma. This is consistent with the fact that although total FN is homogeneously distributed throughout the tumour stroma, the expression of B–FN is confined to certain regions, and it is these areas that had previously been successfully localised (in 95% of cases) in invasive ductal carcinoma using mAb BC-1 (Kaczmarek et al, 1994).

Previous findings in the staining of BC-1 of glioblastoma multiforme tumour have been confirmed. Castellani et al (1994) had observed a typical pattern of staining of glomerular-like vascular structures, and in our experiments, CGS-1 and CGS-2 have been shown to give qualitatively identical results.

There is, however, an important difference between CGS-1 and CGS-2 and the mAb BC-1: the two human scFvs have been demonstrated to bind to both chicken and mouse B–FN, whereas BC-1 is strictly human-specific. CGS-2 reacted with chicken embryos (data not shown) and both CGS-1 and CGS-2 reacted with mouse tumours.

CGS-1 staining of vascular structures on sections of the murine F9 teratocarcinoma has also been shown. In contrast, all normal mouse tissues tested (liver, spleen, kidney, stomach, small intestine, large intestine, ovary, uterus, bladder, pancreas, suprarenal glands, skeletal muscle, heart, lung, thyroid and brain) showed a negative staining reaction with CGS-1 and CGS-2 (data not shown) The structures stained in the F9 teratocarcinoma sections were shown to be ED-B specific by using the recombinant ED-B domain to completely inhibit the staining obtained (data not shown).

Example 5

The Use of Affinity Matured Anti-Ed-B scFvs in in vivo Targeting of Human Tumours The human melanoma cell-line SKMEL-28 was used to develop xenografted tumours in 6-10 weeks old nude mice (Balb-c or MF-1; Harlan UK), by injecting $1 \times 10^7$ cells/mouse subcutaneously in one flank. Mice bearing tumours were injected in the tail vein with 100 µl of 1 mg/ml $scFv_1$-$Cy7_1$, solution in PBS when tumours had reached a diameter of approximately 1 cm.

Labeling of recombinant antibodies with CY7 was achieved by adding 100 µM sodium bicarbonate, pH=9.3, and 200l CY7-bis-OSu (Amersham; Cat. Nr. PA17000; 2 mg/ml in DMSO) to 1 ml antibody solution in PBS (1 mg/ml). After 30 minutes at room temperature, 100 µl 1M Tris, pH=7.4, was added to the mixture and the labeled antibody was separated from unreacted dye using disposable PD10 columns (Pharmacia Biotech, Piscataway, N.J., USA) equilibrated with PBS. The eluted green antibody fractions were concentrated to approximately 1 mg/ml using Centricon-10 tubes (Amicon, Beverly, Mass., USA). The labeling ratio achieved was generally close to one molecule CY7: one molecule antibody. This was estimated spectroscopically with 1 cm cuvettes, assuming that a 1 mg/ml antibody solution gives an absorption of 1.4 units at 280 nm, that the molar extinction coefficient of CY7 at 747 nm is 200'000 ($M^{-1}$ $cm^{-1}$) and neglecting the CY7 absorption at 280 nm. Immunoreactivity of the antibody samples after labeling was confirmed either by bandshift (Neri et al., 1996b), by affinity-chromatography on an antigen column or by BIAcore analysis. Mice were imaged with a home-built mouse-imager at regular time intervals, under anesthaesia by inhalation of an oxygen/fluorothane mixture. Two to eight animals were studied for each sample, in order to ascertain the reproducibility of the results. The procedures were performed according to the UK Project Licence "Tumour Targeting" issued to D. Neri (UK PPL 80/1056).

The infrared mouse-imager was built as a modification of the photodetection system of Folli et al. (1994), that allows the use of the infrared fluorophore CY7. Infrared illumination was chosen in order to obtain better tissue penetration. The fluorescence of CY7 (>760 nm) is invisible to humans and requires the use of a computer-controlled CCD-camera. The mouse-imager consisted of a black-painted, light-tight box, equipped with a 100 W tungsten halogen lamp, fitted with a 50 mm diameter excitation filtre specifically designed for CY7 (Chroma Corporation, Brattleboro, Vt., USA; 673-748 nm). The resulting illumination beam is, to a good approximation, homogenous over an area of 5×10 cm size, in which the mouse was placed for imaging. Fluorescence was detected by an 8-bit monochrome Pulnix CCD-camera, equipped with a C-mount lens and a 50 mm emission filtre (Chroma Corporation, Brattleboro, Vt., USA; 765-855 nm), and interfaced with the ImageDOK system (Kinetic Imaging Ltd., Liverpool, UK). This system consists of a computer, equipped with a frame-grabber and software for the capture and integration of sequential images. Three sequential images acquired in 50 ms each were typically used in the averaging process; this number was kept constant for the series of pictures of one animal, to allow a direct comparison of tumour targeting at different time points. Pictures in TIFF format were then converted to PICT files using the program Graphics Converter, and elaborated using the program MacDraw Pro with a Power Macintosh 7100/66 computer.

A schematic outline of the design of this apparatus is depicted in FIG. 4.

These experiments demonstrated that both scFv's localised to the tumour when visualised at a macroscopic level.

Microscopic demonstration of targeting of neovasculature of developing tumours with the two anti-EDB scFvs was detailed as follows.

Nude mice and/or SCID mice bearing either a xenografted SKMEL-28 human melanoma or a mouse F9 teratocarcinoma in one flank, were injected with either unlabeled scFv fragments with the FLAG tag, or biotinylated scFv fragments.

Mice were sacrificed at different time points after injection, tumour and non-tumour sections obtained, which were then stained with conventional immunohistochemistry protocols, using either the anti-FLAG M2 antibody (Kodak, 181) or streptavidin-based detection reagents. Optimal targeting was generally obtained at 12 hours post injection. Both CGS1 and CGS2 were demonstrated to bind the neovasculature of both the xenografted human tumour and the murine teratocarcinoma.

Example 6

Targeting of Xenografted Murine F9 Teratocarcinoma in Nude Mice

We developed solid tumours in the flank of nude mice by sub-cutaneous injection of $4 \times 10^6$ murine F9 teratocarcinoma cells. This tumour grows very rapidly in mice, reaching 1 cm diameter in approximately one week after injection, and is highly vascularised. To image the targeting of the antibodies, we used a modification of the photodetection methodology of Folli et al (1994), which allows a kinetic evaluation of tumour targeting and of antibody clearance on the same animal imaged at various time points, as is described in detail above (see FIG. 4).

For targeting to the tumour and to facilitate detection of the antibodies, scFv(CGS-1), scFv (CGS-2) and the anti-lysozyme scFv (D1.3) (McCafferty et al., 1990) were appended with a homodimerisation tag (Pack et al., 1993) by subcloning the antibodies in the Sfi1/Not1 sites of the expression Vector pGIN50. This vector is a derivative of pDN268 (Neri et al., 1996b), in which the His6 (SEQ ID NO: 15) sequence of the tag is replaced by the sequence: GGC LTD TLQ AFT DQL EDE KSA LQT EIA HLL KEK EKL EFI LAA H (SEQ ID NO: 16), which contains a cysteine residue and the amphipatic helix of the Fos protein for the covalent homodimerisation of antibody fragments (Abate et al. 1990). Complete covalent dimerisation was not achieved: approximately 30-50% of the antibody fragments consisted of covalently-linked dimers.

Antibody fragments were purified by affinity-chromatography on columns obtained by coupling hen egg lysozyme (D1.3) or 7B89 (anti-ED-B antibodies; Carnemolla et al., 1996) to CNBr-activated Sepharose (Pharmacia Biotech, Piscataway, N.J., USA). Supernatants were loaded onto the affinity supports, which were then washed with PBS, with PBS+0.5 M NaCl and eluted with 100 mM Et3N. The antibodies were then dialysed against PBS.

The antibodies were labeled as described above and were then injected in the tail vein of tumour-bearing mice with 100 µl of 1 mg/ml scFv$_1$-Cy7$_1$, solution in PBS, when the tumours had reached a diameter of approximately 1 cm.

As shown in FIG. 5, scFv(CGS-1) localised on the tumour for up to three days, though there was also rapid clearance from the tumour during this period. However there was also some staining of the femur. The targeting performance of CGS-1 to the tumour was dramatically improved by introducing an amphipathic helix containing a cysteine residue at the C-terminus to promote antibody dimerisation (Pack et al., 1993). Indeed the localisation of the dimeric scFv(CGS-2)$_2$ did not appear to significantly decrease from 24 to 72 hours. By contrast, a negative control (the dimeric antibody scFv (D1.3)$_2$, anti-lysozyme antibody), showed a rapid clearance and no detectable localisation on the tumour or femur.

ScFv(28SI) showed weak tumour targeting at 6 hours (not shown) but none was detectable at 24 hours or later (FIG. 6). Affinity maturation led to much improved targeting; thus scFv(CGS-2) targeted small and large F9 tumours efficiently, whether as monomer (FIG. 6) or dimer (not shown). After two days, the percent injected dose of antibody per gram of tumour was found to be about 2 for the scFv(CGS-2) monomer and 3-4 for the scFv(CGS-2) dimer. The dose delivered to the tumour by scFv(CGS-2) was also higher than for scFv (CGS-1) (FIGS. 5 and 6), and correlates with their respective affinities (Table 1). However, both scFv(28SI) and scFv (CGS-2) appear to be prone to proteolytic cleavage and show a high liver uptake (FIG. 6), whereas scFv(CGS-1) antibodies were significantly more stable and show lower liver uptake (FIG. 5).

REFERENCES

Ausubel et al. eds., John Wiley & Sons, 1992; Short Protocols in Molecular Biology, Second Edition.
Alitalo et al. Adv. Cancer Res. 37, 111-158 (1982).
Bagshawe K. D. et al. (1991) Antibody, Immunoconjugates and Radiopharmaceuticals 4: 915-922.
Barone et al. EMBO J. 8, 1079-1085 (1989).
Bird et al, Science, 242, 423-426, (1988).
Borsi et al. J. Cell. Biol. 104, 595-600 (1987).
Borsi et al. Anal. Biochem. 192, 372-379 (1991).
Borsi et al. Int. J. Cancer 52, 688-692 (1992a).
Borsi et al. Exp. Cell Res. 199, 98-105 (1992b).
Brown et al. Amer. J. Pathol. 142, 793-801 (1993).
Carnemolla et al. J. Cell Biol. 108, 1139-1148 (1989).
Carnemolla et al. J. Biol. Chem. 24689-24692 (1992).
Castellani et al. J. Cell. Biol. 103, 1671-1677 (1986).
Castellani et al. Int. J. Cancer 59, 612-618 (1994).
Crothers et al. Immunochemistry 9, 341-357 (1972).
DeJager et al (1988) Proc. Am. Assoc. Cancer Res. 29:377.
Folli, et al (1994), Cancer Res., 54, 2643-2649.
Ffrench-Constant et al. J. Cell Biol. 109, 903-914 (1989).
Ffrench-Constant et al. Development 106, 375-388 (1989).
Gibson T J (1984) PhD thesis. (University of Cambridge, Cambridge, UK).
Griffiths, et al. (1994), EMBO J. 13, 3245-3260.
Gutman and Kornblihtt. Proc. Natl. Acad. Sci. (USA) 84, 7179-7182 (1987).
Hawkins et al. J. Mol. Biol. 226, 889-896 (1992).
Holliger et al Proc. Natl. Acad. Sci. USA 90 6444-6448, 1993).
Holliger, P. and Winter G. Current Opinion Biotechnol. 4, 446-449 (1993).
Hoogenboom et al. Nucl. Acids Res 19, 4133-4137 (1991).
Humphries et al. J. Cell Biol. 103, 2637-2647 (1986).
Huston et al, PNAS USA, 85, 5879-5883, (1988)
Hynes Ann. Rev. Cell Biol. 1, 67-90 (1985).
Jain R K. Sci. Am. 271, 58-65 (1994).
Jonsson et al. BioTechniques 11, 620-627 (1991).

Juweid et al. Cancer Res 52, 5144-5153 (1992).
Kaczmarek et al. Int. J. Cancer 58, 11-16 (1994).
Kornblihtt et al. EMBO J. 4, 1755 (1985).
Laitinen et al. Lab. Invest. 64, 375-388 (1991).
Ledermann J. A. et al. (1991) Int J. Cancer 47: 659-664; Low et al (1996), J. Mol. Biol., 260, 359-368.
Marks et al (1991), J. Mol. Biol., 222, 581-597.
Marks et al, (1992), Bio/Technology, 10, 779-783.
McCafferty, J., Griffiths, A. D., Winter, G., Chiswell, D. J. (1990) Phage antibodies: filamentous phage displaying antibody variable domains. Nature (London), 348, 552-554.
Neri et al (1996a), Bio/Techniques, 20, 708-713.
Neri et al (1996b), Nature Biotechnology, 14, 385-390.
Nissim et al. EMBO J. 13, 692-698 (1994).
Norton and Hynes. Mol. Cell. Biol. 7, 4297-4307 (1987).
Owens et al. Oxf. Surv. Eucaryot. Genes 3, 141-160 (1986).
Oyama et al. J. Biol. Chem. 10331-10334 (1989).
Oyama et al. Cancer Res. 50, 1075-1078 (1990).
Pack et al (1993), Bio/Technology, 11, 1271-1277.
Peters et al. Cell Adhes. Commun. 3, 67-89 (1995).
Pierschbacher et al. Cell 26, 259-267 (1981).
Pluckthun, A. Bio/Technology 9: 545-551 (1991).
Reff, M. E. (1993) Curr. Opinion Biotech. 4: 573-576.
Ruoslahti. Ann. Rev. Biochem. 57, 375-413 (1988).
Saginati et al. Eur J. Biochem. 205, 545-549 (1992).
Schwarzbauer et al. EMBO J. 6, 2573-2580 (1987).
Schroff et al, 1985 Cancer Res 45: 879-885.
Siri et al. Nucl. Acids Res. 19, 525-531 (1991).
Tomlinson I. M. et al, (1992) J. Mol. Biol. 227: 776-798.
Traunecker et al, Embo Journal, 10, 3655-3659, (1991).
Trill J. J. et al. (1995) Curr. Opinion Biotech 6: 553-560.
Vartio et al. J. Cell Science 88, 419-430 (1987).
Vaughan et al (1996), Nature Biotechnol., 14, 309-314.
Ward, E. S. et al., Nature 341, 544-546 (1989).
Winter, G and C. Milstein, Nature 349, 293-299, 1991.
WO94/13804 Yamada. Ann. Rev. Biochem. 52, 761-799 (1983).
Zardi et al. EMBO J. 6, 2337-2342 (1987).

The invention claimed is:

1. A method for targeting the ED-B oncofoetal domain of fibronectin (FN), in a subject in need thereof, comprising
administering an effective amount of an antibody or an antigen-binding fragment thereof which is optionally coupled, bound or engineered as a fusion protein to possess an effector function,
wherein said antibody or said antigen-binding fragment thereof is specific for and binds directly to the ED-B oncofoetal domain of fibronectin (FN).

2. A method according to claim 1 for targeting a tumor expressing or associated with the ED-B oncofoetal domain of fibronectin.

3. A method according to claim 2 for the diagnosis of a tumor in a subject in need thereof, comprising
administering an effective amount of an antibody or an antigen-binding fragment thereof which is specific for and binds directly to the ED-B oncofoetal domain of fibronectin (FN), wherein said antibody or said antigen-binding fragment thereof is tagged with a reporter molecule,
wherein detection of ED-B expression via binding of said antibody or said antigen-binding fragment thereof thereto is indicative of the presence of said tumor.

4. A method according to claim 2 for the therapy of a tumor in a subject in need thereof, comprising administering an effective amount of an antibody or an antigen-binding fragment thereof which is specific for and binds directly to the ED-B oncofoetal domain of fibronectin (FN), wherein said antibody or said antigen-binding fragment thereof is coupled, bound or engineered as a fusion protein to possess an effector function which is targeting of a toxin or radioactivity to a tumor expressing or associated with said ED-B oncofetal domain of fibronectin (FN).

5. A method according to claim 2, wherein said antibody or said antigen-binding fragment thereof is coupled, bound or engineered as a fusion protein to possess an effector function which is targeting of a toxin or radioactivity to a tumor expressing or associated with said ED-B oncofoetal domain of fibronectin (FN).

6. The method according to claim 2, wherein said antibody or said antigen-binding fragment thereof comprises a variable heavy (VH) chain comprising amino acids 1-98 of the polypeptide sequence set forth in SEQ ID NO: 8 and the CDR3 sequence set forth in SEQ ID NO: 12 (Ser Leu Pro Lys).

7. The method according to claim 2, wherein said antibody or said antigen-binding fragment thereof comprises a variable heavy (VH) chain comprising amino acids 1-98 of the polypeptide sequence set forth in SEQ ID NO: 9 and the CDR3 sequence set forth in SEQ ID NO: 1 (Gly Val Gly Ala Phe Arg Pro Tyr Arg Lys His Glu).

8. The method according to claim 2, wherein said antibody or said antigen-binding fragment thereof comprises a variable light (VL) chain comprising amino acids 1-90 of the polypeptide sequence set forth in SEQ ID NO: 10 and the CDR3 sequence set forth in SEQ ID NO: 13 (Pro Val Val Leu Asn Gly Val Val).

9. The method according to claim 2, wherein said antibody or said antigen-binding fragment thereof comprises a variable light (VL) chain comprising amino acids 1-90 of the polypeptide sequence set forth in SEQ ID NO: 11 and the CDR3 sequence set forth in SEQ ID NO: 14 (Pro Phe Glu His Asn Leu Val Val).

10. The method according to claim 2, wherein said antibody or said antigen-binding fragment thereof comprises a variable heavy (VH) chain comprising
(a) amino acids 1-98 of the polypeptide sequence set forth in SEQ ID NO: 8; or
(b) amino acids 1-98 of the polypeptide sequence set forth in SEQ ID NO: 9; and
the CDR3 sequence.

11. The method according to claim 2, wherein said antibody or said antigen-binding fragment thereof as a purified monomer has a dissociation constant ($K_d$) of $6 \times 10^{-8}$M or less for ED-B FN.

12. The method according to claim 2, wherein said antigen-binding fragment thereof is an $scF_v$ molecule which is specific for and binds directly to the ED-B oncofoetal domain of fibronectin (FN).

13. The method according to claim 2, wherein said antigen-binding fragment thereof is a dimeric $scF_v$ molecule which is specific for and binds directly to the ED-B oncofoetal domain of fibronectin (FN).

14. The method according to claim 2, wherein said antibody or said antigen-binding fragment thereof comprises a CGS-1 sequence set forth in SEQ ID NO: 8 or SEQ ID NO: 10 or a CGS-2 sequence set forth in SEQ ID NO: 9 or SEQ ID NO: 11.

15. The method according to claim 2, wherein the subject is human.

16. The method according to claim 2, wherein the tumor is a tumor which expresses or is associated with ED-B.

17. The method according to claim 2, wherein the tumor comprises elevated expression of said ED-B onofoetal domain of fibronectin (FN).

18. The method according to claim 2, wherein the tumor is a solid tumor.

19. The method according to claim 2, wherein the tumor is melanoma, ductal carcinoma or teratocarcinoma.

20. The method according to claim 2, wherein said antibody or said antigen-binding fragment thereof is coupled, bound or engineered as a fusion protein to possess an effector function which is a reporter molecule.

21. The method of claim 1 wherein said antibody is of the IgG subtype.

22. The method of claim 2 wherein said antibody is of the IgG subtype.

23. The method of claim 4 wherein said antibody is of the IgG subtype.

* * * * *